(12) United States Patent
Li et al.

(10) Patent No.: US 7,074,618 B2
(45) Date of Patent: Jul. 11, 2006

(54) ADENOVIRAL E1A/E1B COMPLEMENTING CELL LINE

(75) Inventors: Yuanhao Li, Palo Alto, CA (US); Deborah Farson, Belmont, CA (US); Luqun Tao, Foster City, CA (US); De-Chao Yu, Foster City, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 10/857,137

(22) Filed: May 28, 2004

(65) Prior Publication Data

US 2005/0003506 A1 Jan. 6, 2005

Related U.S. Application Data

(63) Continuation-in-part of application No. 10/613,106, filed on Jul. 3, 2003.

(51) Int. Cl.
*C12N 15/861* (2006.01)
*C12N 15/867* (2006.01)
*C12N 5/10* (2006.01)
*C12N 15/63* (2006.01)
*C12N 15/64* (2006.01)

(52) U.S. Cl. .............. 435/455; 435/325; 435/366; 435/371; 435/320.1

(58) Field of Classification Search ............... 435/325, 435/366, 371, 455, 456, 69.1
See application file for complete search history.

(56) References Cited

U.S. PATENT DOCUMENTS

| | | | |
|---|---|---|---|
| 5,891,690 A | 4/1999 | Massie | |
| 5,994,128 A | 11/1999 | Fallaux et al. | |
| 6,265,212 B1 | 7/2001 | Fallaux et al. | |
| 2001/0049136 A1* | 12/2001 | Imler et al. | 435/320.1 |

FOREIGN PATENT DOCUMENTS

| | | |
|---|---|---|
| WO | WO 95/34671 | 12/1995 |
| WO | WO 96/17053 | 6/1996 |
| WO | WO 96/18418 | 6/1996 |

OTHER PUBLICATIONS

Berkner et al., Development of Adenovirus Vectors for the Expression of Heterologous Genes, Biotechniques, 1988, 6: 616-629.

Fallaux et al., "New Helper Cells and Matched Early Region 1-Deleted Adenovirus Vectors Prevent Generation of Replication-Component Adenoviruses," Human Gene Therapy, 1998, 9:1909-1917.

Graham et al., "Characteristics of a Human Cell Line Transformed by DNA from Human Adenovirus Type 5," J. General Virology, 1977, 36:59-72.

Kim et al, "Development of a packaging cell line for propagation of replication-deficient adenovirus vector", Exp. Mol. Med., 2001, 33(3)145-9.

Kozarsky et al., "Gene therapy: adenovirus vectors," Curr. Opin. Genet. Dev., 1993, 3: 499-503.

Schiedner et al., "Efficient Transformation of Primary Human Amniocytes by E1 Functions of Ad5: Generation of New Cell Lines for Adenoviral Vector Production," Human Gene Therapy, 2000, 11:2105-2116.

Yu et al., "Selectively replicating oncolytic adenoviruses as cancer therapeutics," Curr. Opin. Mol. Ther., 2002, 4(5):435-443.

Gorziglia, et al., "Elimination of both E1 and E2a from Adenovirus Vectors Further Improves Prospects for In Vivo Human Gene Therapy", Journal of Virology, vol. 70, No. 6, pp. 4173-4178, 1996.

Murakami, et al., "A Single Short Stretch of Homology Between Adenoviral Vector and Packaging Cell Line Can Give Rise to Cytopathic Effect-Inducing, Helper-Dependent E1-Positive Particles", Human Gene Therapy, vol. 13, pp. 909-920, 2002.

Louis, et al., "Cloning and Sequencing of the Cellular-Viral Junctions from the Human Adenovirus Type 5 Transformed 293 Cell Line", Virology, vol. 233, pp. 423-429, 1997.

Hehir, et al., "Molecular Characterization of Replication-Competent Variants of Adenovirus Vectors and Genome Modifications To Prevent Their Occurrence", Journal of Virology, vol. 70, No. 12, pp. 8459-8467, 1996.

* cited by examiner

*Primary Examiner*—David Guzo
(74) *Attorney, Agent, or Firm*—DLA Piper Rudnick Gray Cary US LLP

(57) ABSTRACT

Adenovirus packaging cell lines for growth of E1A/E1B deficient adenovirus that is substantially free of replication competent adenovirus (RCA), are provided. Methods for producing adenovirus substantially free of RCA are also provided, wherein the adenovirus is grown in a cell line containing coding sequences for adenovirus E1A and E1B, are operably linked to promoters that lack polynucleotide sequences sharing substantial sequence identity with the native adenovirus E1A and E1B promoters.

10 Claims, 9 Drawing Sheets

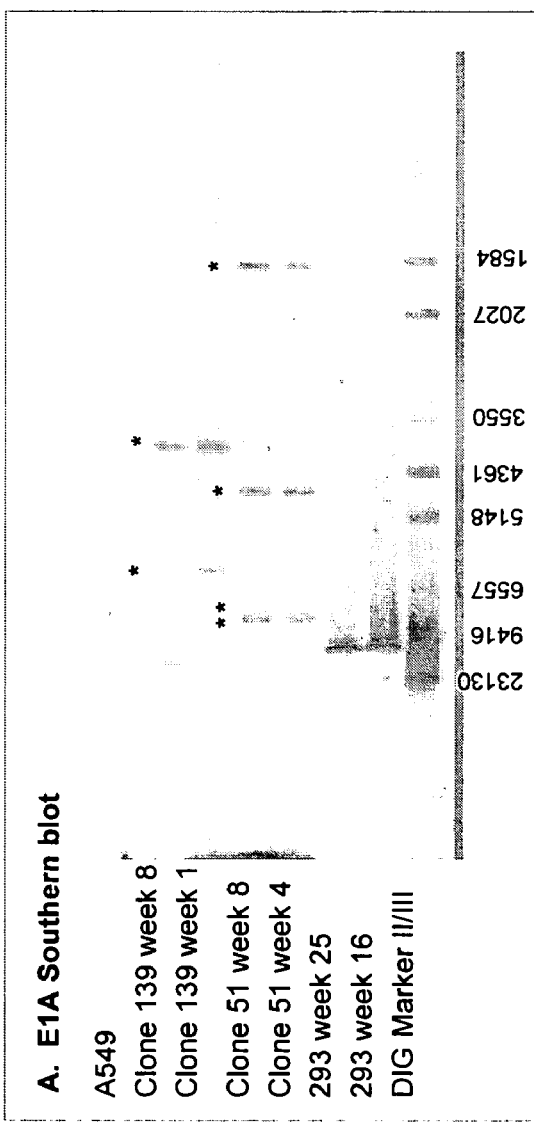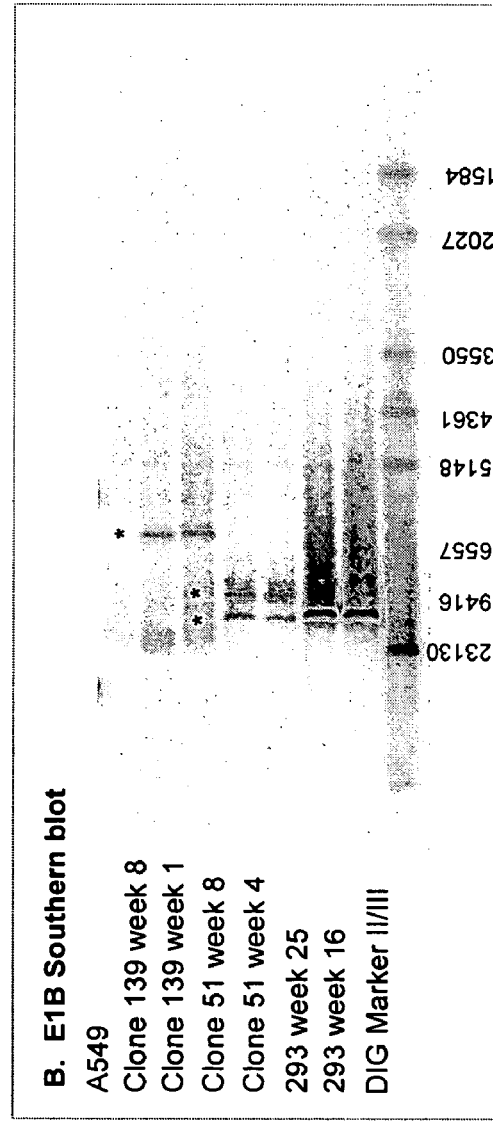
Fig. 4A
Fig. 4B

SEQUENCE LISTING

```
<160> NUMBER OF SEQ ID NOS: 8

<210> SEQ ID NO 1
<211> LENGTH: 986
<212> TYPE: DNA
<213> ORGANISM: adenovirus

<400> SEQUENCE: 1
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttttcc cgactctgta atgttggcgg tgcaggaagg gattgactta     240
ctcacttttc cgccggcgcc cggttctccg gagccgcctc acctttcccg gcagcccgag     300
cagccggagc agagagcctt gggtccggtt tctatgccaa accttgtacc ggaggtgatc     360
gatcttacct gccacgaggc tggctttcca cccagtgacg acgaggatga agagggtgag     420
gagtttgtgt tagattatgt ggagcacccc gggcacggtt gcaggtcttg tcattatcac     480
cggaggaata cggggggaccc agatattatg tgttcgcttt gctatatgag gacctgtggc     540
atgtttgtct acagtaagtg aaaattatgg gcagtgggtg atagagtggt gggtttggtg     600
tggtaatttt tttttttaatt tttacagttt tgtggtttaa agaattttgt attgtgattt     660
ttttaaaagg tcctgtgtct gaacctgagc ctgagcccga gccagaaccg gagcctgcaa     720
gacctacccg ccgtcctaaa atggcgcctg ctatcctgag acgcccgaca tcacctgtgt     780
ctagagaatg caatagtagt acggatagct gtgactccgg tccttctaac acacctcctg     840
agatacaccc ggtggtcccg ctgtgcccca ttaaaccagt tgccgtgaga gttggtgggc     900
gtcgccaggc tgtggaatgt atcgaggact tgcttaacga gcctgggcaa cctttggact     960
tgagctgtaa acgccccagg ccataa                                          986

<210> SEQ ID NO 2
<211> LENGTH: 289
<212> TYPE: PRT
<213> ORGANISM: adenovirus

<400> SEQUENCE: 2

Met Arg His Ile Ile Cys His Gly Gly Val Ile Thr Glu Glu Met Ala
  1               5                  10                  15

Ala Ser Leu Leu Asp Gln Leu Ile Glu Glu Val Leu Ala Asp Asn Leu
```

-continued

```
                   20                  25                  30
Pro Pro Pro Ser His Phe Glu Pro Pro Thr Leu His Glu Leu Tyr Asp
            35                  40                  45
Leu Asp Val Thr Ala Pro Glu Asp Pro Asn Glu Glu Ala Val Ser Gln
 50                  55                  60
Ile Phe Pro Asp Ser Val Met Leu Ala Val Gln Glu Gly Ile Asp Leu
 65                  70                  75                  80
Leu Thr Phe Pro Pro Ala Pro Gly Ser Pro Glu Pro Pro His Leu Ser
                85                  90                  95
Arg Gln Pro Glu Gln Pro Glu Gln Arg Ala Leu Gly Pro Val Ser Met
            100                 105                 110
Pro Asn Leu Val Pro Glu Val Ile Asp Leu Thr Cys His Glu Ala Gly
            115                 120                 125
Phe Pro Pro Ser Asp Asp Glu Asp Glu Glu Gly Glu Glu Phe Val Leu
            130                 135                 140
Asp Tyr Val Glu His Pro Gly His Gly Cys Arg Ser Cys His Tyr His
145                 150                 155                 160
Arg Arg Asn Thr Gly Asp Pro Asp Ile Met Cys Ser Leu Cys Tyr Met
                165                 170                 175
Arg Thr Cys Gly Met Phe Val Tyr Ser Pro Val Ser Glu Pro Glu Pro
                180                 185                 190
Glu Pro Glu Pro Glu Pro Pro Ala Arg Pro Thr Arg Arg Pro Lys
            195                 200                 205
Met Ala Pro Ala Ile Leu Arg Arg Pro Thr Ser Pro Val Ser Arg Glu
            210                 215                 220
Cys Asn Ser Ser Thr Asp Ser Cys Asp Ser Gly Pro Ser Asn Thr Pro
225                 230                 235                 240
Pro Glu Ile His Pro Val Val Pro Leu Cys Pro Ile Lys Pro Val Ala
                245                 250                 255
Val Arg Val Gly Gly Arg Arg Gln Ala Val Glu Cys Ile Glu Asp Leu
                260                 265                 270
Leu Asn Glu Pro Gly Gln Pro Leu Asp Leu Ser Cys Lys Arg Pro Arg
                275                 280                 285
Pro

<210> SEQ ID NO 3
<211> LENGTH: 243
<212> TYPE: PRT
<213> ORGANISM: adenovirus

<400> SEQUENCE: 3

Met Arg His Ile Ile Cys His Gly Gly Val Ile Thr Glu Glu Met Ala
 1               5                  10                  15
Ala Ser Leu Leu Asp Gln Leu Ile Glu Glu Val Leu Ala Asp Asn Leu
            20                  25                  30
Pro Pro Pro Ser His Phe Glu Pro Pro Thr Leu His Glu Leu Tyr Asp
            35                  40                  45
Leu Asp Val Thr Ala Pro Glu Asp Pro Asn Glu Glu Ala Val Ser Gln
 50                  55                  60
Ile Phe Pro Asp Ser Val Met Leu Ala Val Gln Glu Gly Ile Asp Leu
 65                  70                  75                  80
Leu Thr Phe Pro Pro Ala Pro Gly Ser Pro Glu Pro Pro His Leu Ser
                85                  90                  95
Arg Gln Pro Glu Gln Pro Glu Gln Arg Ala Leu Gly Pro Val Ser Met
```

```
            100                 105                 110
Pro Asn Leu Val Pro Glu Val Ile Asp Leu Thr Cys His Glu Ala Gly
            115                 120                 125

Phe Pro Pro Ser Asp Asp Glu Asp Glu Glu Gly Pro Val Ser Glu Pro
        130                 135                 140

Glu Pro Glu Pro Glu Pro Glu Pro Ala Arg Pro Thr Arg Arg
145                 150                 155                 160

Pro Lys Met Ala Pro Ala Ile Leu Arg Arg Pro Thr Ser Pro Val Ser
                165                 170                 175

Arg Glu Cys Asn Ser Ser Thr Asp Ser Cys Asp Ser Gly Pro Ser Asn
            180                 185                 190

Thr Pro Pro Glu Ile His Pro Val Val Pro Leu Cys Pro Ile Lys Pro
            195                 200                 205

Val Ala Val Arg Val Gly Gly Arg Arg Gln Ala Val Glu Cys Ile Glu
            210                 215                 220

Asp Leu Leu Asn Glu Pro Gly Gln Pro Leu Asp Leu Ser Cys Lys Arg
225                 230                 235                 240

Pro Arg Pro

<210> SEQ ID NO 4
<211> LENGTH: 2144
<212> TYPE: DNA
<213> ORGANISM: Adenovirus

<400> SEQUENCE: 4
gccgtgggct aatcttggtt acatctgacc tcatggaggc ttgggagtgt ttggaagatt     60
tttctgctgt gcgtaacttg ctggaacaga gctctaacag tacctcttgg ttttggaggt    120
ttctgtgggg ctcatcccag gcaaagttag tctgcagaat taaggaggat tacaagtggg    180 aattttgaaga gcttttgaaa tcctgtggtg agctgtttga ttctttgaat ctgggtcacc    240
aggcgctttt ccaagagaag gtcatcaaga ctttggattt ttccacaccg gggcgcgctg    300
cggctgctgt tgctttttttg agttttataa aggataaatg gagcgaagaa acccatctga    360 gcgggggta cctgctggat tttctggcca tgcatctgtg gagagcggtt gtgagacaca    420
agaatcgcct gctactgttg tcttccgtcc gcccggcgat aataccgacg gaggagcagc    480
agcagcagca ggaggaagcc aggcggcggc ggcaggagca gagcccatgg aacccgagag    540
ccggcctgga ccctcgggaa tgaatgttgt acaggtggct gaactgtatc cagaactgag    600
acgcattttg acaattacag aggatgggca ggggctaaag ggggtaaaga gggagcgggg    660
ggcttgtgag gctacagagg aggctaggaa tctagctttt agcttaatga ccagacaccg    720
tcctgagtgt attactttc aacagatcaa ggataattgc gctaatgagc ttgatctgct    780
ggcgcagaag tattccatag agcagctgac cacttactgg ctgcagccag gggatgattt    840
tgaggaggct attagggtat atgcaaaggt ggcacttagg ccagattgca agtacaagat    900
cagcaaactt gtaaatatca ggaattgttg ctacatttct gggaacgggg ccgaggtgga    960
gatagatacg gaggataggg tggcctttag atgtagcatg ataaatatgt ggccgggggt   1020
gcttggcatg gacggggtgg ttattatgaa tgtaaggttt actggcccca atttttagcgg   1080 tacggttttc ctggccaata ccaaccttat cctacacggt gtaagcttct atgggtttaa   1140
caatacctgt gtggaagcct ggaccgatgt aagggttcgg ggctgtgcct tttactgctg   1200
ctggaagggg gtggtgtgtc gccccaaaag cagggcttca attaagaaat gcctctttga   1260
aaggtgtacc ttgggtatcc tgtctgaggg taactccagg gtgcgccaca atgtggcctc   1320
```

-continued

```
cgactgtggt tgcttcatgc tagtgaaaag cgtggctgtg attaagcata acatggtatg    1380
tggcaactgc gaggacaggg cctctcagat gctgacctgc tcggacggca actgtcacct    1440
gctgaagacc attcacgtag ccagccactc tcgcaaggcc tggccagtgt ttgagcataa    1500
catactgacc cgctgttcct tgcatttggg taacaggagg ggggtgttcc taccttacca    1560
atgcaatttg agtcacacta agatattgct tgagcccgag agcatgtcca aggtgaacct    1620
gaacggggtg tttgacatga ccatgaagat ctggaaggtg ctgaggtacg atgagacccg    1680
caccaggtgc agaccctgcg agtgtggcgg taaacatatt aggaaccagc ctgtgatgct    1740
ggatgtgacc gaggagctga ggcccgatca cttggtgctg gcctgcaccc gcgctgagtt    1800
tggctctagc gatgaagata cagattgagg tactgaaatg tgtgggcgtg gcttaagggt    1860
gggaaagaat atataaggtg ggggtcttat gtagttttgt atctgttttg cagcagccgc    1920
cgccgccatg agcaccaact cgtttgatgg aagcattgtg agctcatatt tgacaacgcg    1980
catgccccca tgggccgggg tgcgtcagaa tgtgatgggc tccagcattg atggtcgccc    2040
cgtcctgccc gcaaactcta ctaccttgac ctacgagacc gtgtctggaa cgccgttgga    2100
gactgcagcc tccgccgccg cttcagccgc tgcagccacc gccc                    2144
```

<210> SEQ ID NO 5
<211> LENGTH: 176
<212> TYPE: PRT
<213> ORGANISM: adenovirus

<400> SEQUENCE: 5

Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Ser Ser Val Arg Pro Ala Ile Ile
    130                 135                 140

Pro Thr Glu Glu Gln Gln Gln Gln Glu Glu Ala Arg Arg Arg
145                 150                 155                 160

Gln Glu Gln Ser Pro Trp Asn Pro Arg Ala Gly Leu Asp Pro Arg Glu
                165                 170                 175

<210> SEQ ID NO 6
<211> LENGTH: 496
<212> TYPE: PRT
<213> ORGANISM: adenovirus

<400> SEQUENCE: 6

Met Glu Arg Arg Asn Pro Ser Glu Arg Gly Val Pro Ala Gly Phe Ser

-continued

```
  1               5                  10                 15
Gly His Ala Ser Val Glu Ser Gly Cys Glu Thr Gln Glu Ser Pro Ala
             20                  25                 30
Thr Val Val Phe Arg Pro Pro Gly Asp Asn Thr Asp Gly Gly Ala Ala
             35                  40                 45
Ala Ala Ala Gly Gly Ser Gln Ala Ala Ala Gly Ala Glu Pro Met
             50                  55                 60
Glu Pro Glu Ser Arg Pro Gly Pro Ser Gly Met Asn Val Val Gln Val
 65              70                  75                 80
Ala Glu Leu Tyr Pro Glu Leu Arg Arg Ile Leu Thr Ile Thr Glu Asp
             85                  90                 95
Gly Gln Gly Leu Lys Gly Val Lys Arg Glu Arg Gly Ala Cys Glu Ala
             100                 105                110
Thr Glu Glu Ala Arg Asn Leu Ala Phe Ser Leu Met Thr Arg His Arg
             115                 120                125
Pro Glu Cys Ile Thr Phe Gln Gln Ile Lys Asp Asn Cys Ala Asn Glu
             130                 135                140
Leu Asp Leu Leu Ala Gln Lys Tyr Ser Ile Glu Gln Leu Thr Thr Tyr
145              150                 155                160
Trp Leu Gln Pro Gly Asp Asp Phe Glu Glu Ala Ile Arg Val Tyr Ala
             165                 170                175
Lys Val Ala Leu Arg Pro Asp Cys Lys Tyr Lys Ile Ser Lys Leu Val
             180                 185                190
Asn Ile Arg Asn Cys Cys Tyr Ile Ser Gly Asn Gly Ala Glu Val Glu
             195                 200                205
Ile Asp Thr Glu Asp Arg Val Ala Phe Arg Cys Ser Met Ile Asn Met
 210             215                220
Trp Pro Gly Val Leu Gly Met Asp Gly Val Val Ile Met Asn Val Arg
 225             230                 235                240
Phe Thr Gly Pro Asn Phe Ser Gly Thr Val Phe Leu Ala Asn Thr Asn
             245                 250                255
Leu Ile Leu His Gly Val Ser Phe Tyr Gly Phe Asn Asn Thr Cys Val
             260                 265                270
Glu Ala Trp Thr Asp Val Arg Val Arg Gly Cys Ala Phe Tyr Cys Cys
             275                 280                285
Trp Lys Gly Val Val Cys Arg Pro Lys Ser Arg Ala Ser Ile Lys Lys
 290             295                 300
Cys Leu Phe Glu Arg Cys Thr Leu Gly Ile Leu Ser Glu Gly Asn Ser
 305             310                 315                320
Arg Val Arg His Asn Val Ala Ser Asp Cys Gly Cys Phe Met Leu Val
             325                 330                335
Lys Ser Val Ala Val Ile Lys His Asn Met Val Cys Gly Asn Cys Glu
             340                 345                350
Asp Arg Ala Ser Gln Met Leu Thr Cys Ser Asp Gly Asn Cys His Leu
             355                 360                365
Leu Lys Thr Ile His Val Ala Ser His Ser Arg Lys Ala Trp Pro Val
             370                 375                380
Phe Glu His Asn Ile Leu Thr Arg Cys Ser Leu His Leu Gly Asn Arg
385              390                 395                400
Arg Gly Val Phe Leu Pro Tyr Gln Cys Asn Leu Ser His Thr Lys Ile
             405                 410                415
Leu Leu Glu Pro Glu Ser Met Ser Lys Val Asn Leu Asn Gly Val Phe
             420                 425                430
```

```
Asp Met Thr Met Lys Ile Trp Lys Val Leu Arg Tyr Asp Glu Thr Arg
        435                 440                 445

Thr Arg Cys Arg Pro Cys Glu Cys Gly Gly Lys His Ile Arg Asn Gln
    450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495

<210> SEQ ID NO 7
<211> LENGTH: 873
<212> TYPE: DNA
<213> ORGANISM: Adenovirus

<400> SEQUENCE: 7
atgagacata ttatctgcca cggaggtgtt attaccgaag aaatggccgc cagtcttttg      60
gaccagctga tcgaagaggt actggctgat aatcttccac ctcctagcca ttttgaacca     120
cctaccttc acgaactgta tgatttagac gtgacggccc ccgaagatcc caacgaggag     180
gcggtttcgc agattttcc cgactctgta atgttggcgg tgcaggaagg gattgactta     240
ctcacttttc cgccggcgcc cggttctccg gagccgcctc acctttcccg gcagcccgag     300
cagccggagc agagagcctt gggtccggtt tctatgccaa accttgtacc ggaggtgatc     360
gatcttacct gccacgaggc tggctttcca cccagtgacg acgaggatga agagggtgag     420
gagtttgtgt tagattatgt ggagcacccc gggcacggtt gcaggtcttg tcattatcac     480
cggaggaata cggggacccc agatattatg tgttcgcttt gctatatgag gacctgtggc     540
atgtttgtct acagtaagcc tgtgtctgaa cctgagcctg agcccgagcc agaaccggag     600
cctgcaagac ctacccgccg tcctaaaatg gcgcctgcta tcctgagacg cccgacatca     660
cctgtgtcta gagaatgcaa tagtagtacg gatagctgtg actccggtcc ttctaacaca     720
cctcctgaga tacaccggt ggtcccgctg tgccccatta aaccagttgc cgtgagagtt     780
ggtgggcgtc gccaggctgt ggaatgtatc gaggacttgc ttaacgagcc tgggcaacct     840
ttggacttga gctgtaaacg ccccaggcca taa                                  873

<210> SEQ ID NO 8
<211> LENGTH: 1491
<212> TYPE: DNA
<213> ORGANISM: Adenovirus

<400> SEQUENCE: 8
atggagcgaa gaaacccatc tgagcggggg gtacctgctg gattttctgg ccatgcatct      60
gtggagagcg gttgtgagac acaagaatcg cctgctactg ttgtcttccg tccgcccggc     120
gataataccg acggaggagc agcagcagca gcaggaggaa gccaggcggc ggcggcagga     180
gcagagccca tggaacccga gagccggcct ggaccctcgg gaatgaatgt tgtacaggtg     240
gctgaactgt atccagaact gagacgcatt ttgacaatta cagaggatgg gcaggggcta     300
aaggggtaa agagggagcg gggggcttgt gaggctacag aggaggctag gaatctagct     360
tttagcttaa tgaccagaca ccgtcctgag tgtattactt tcaacagat caaggataat     420
tgcgctaatg agcttgatct gctggcgcag aagtattcca tagagcagct gaccacttac     480
tggctgcagc cagggatga ttttgaggag gctattaggg tatatgcaaa ggtggcactt     540
aggccagatt gcaagtacaa gatcagcaaa cttgtaaata tcaggaattg ttgctacatt     600
```

```
tctgggaacg gggccgaggt ggagatagat acggaggata gggtggcctt tagatgtagc    660
atgataaata tgtggccggg ggtgcttggc atggacgggg tggttattat gaatgtaagg    720
tttactggcc ccaattttag cggtacggtt ttcctggcca ataccaacct tatcctacac    780
ggtgtaagct tctatgggtt taacaatacc tgtgtggaag cctggaccga tgtaagggtt    840
cggggctgtg cctttactg ctgctggaag ggggtggtgt gtcgcccaa aagcagggct     900 tcaattaaga aatgcctctt tgaaaggtgt accttggta tcctgtctga gggtaactcc    960
agggtgcgcc acaatgtggc ctccgactgt ggttgcttca tgctagtgaa aagcgtggct   1020
gtgattaagc ataacatggt atgtggcaac tgcgaggaca gggcctctca gatgctgacc   1080
tgctcggacg gcaactgtca cctgctgaag accattcacg tagccagcca ctctcgcaag   1140
gcctggccag tgtttgagca taacatactg acccgctgtt ccttgcattt gggtaacagg   1200
aggggggtgt tcctaccta ccaatgcaat ttgagtcaca ctaagatatt gcttgagccc    1260
gagagcatgt ccaaggtgaa cctgaacggg gtgtttgaca tgaccatgaa gatctggaag   1320
gtgctgaggt acgatgagac ccgcaccagg tgcagaccct gcgagtgtgg cggtaaacat   1380
attaggaacc agcctgtgat gctggatgtg accgaggagc tgaggcccga tcacttggtg   1440
ctggcctgca cccgcgctga gtttggctct agcgatgaag atacagattg a            1491
```

US 7,074,618 B2

ADENOVIRAL E1A/E1B COMPLEMENTING CELL LINE

The present application claims priority to U.S. application Ser. No. 10/613,106 filed Jul. 3, 2003, the contents of which are hereby incorporated by reference in their entirety.

FIELD OF THE INVENTION

The invention relates to novel packaging cell lines useful for the production of recombinant adenoviral vectors, including replication competent adenoviral vectors, oncolytic adenoviral vectors, and replication defective adenoviral vectors with E1 early gene region deletions.

BACKGROUND

Vector-mediated transgene delivery finds utility in the treatment of genetic disorders by supplementing a protein or other substance which, is either absent, or present in insufficient amounts in the host. Adenoviral (Ad) vectors are highly efficient vehicles for transgene delivery. Adenoviral-based gene-transfer vectors have a number of features that make them particularly useful for gene transfer into cells including the fact that the biology of adenovirus is well characterized, adenovirus is not associated with any known human disease, adenovirus is efficient in introducing its DNA into host cells, the virus has a broad host cell range and large scale production has been accomplished. Human adenoviral-based vectors, in which at least the E1 region has been deleted and replaced by a gene of interest have been used extensively for gene therapy. Adenovirus vectors currently used in gene therapy are typically replication incompetent and have a deletion in the E1 region.

The features which make recombinant adenoviruses potentially powerful gene delivery vectors have been extensively reviewed (Berkner, *Biotechniques* 6: 616–629, (1988) and Kozarsky & Wilson, *Curr. Opin. Genet Dev.* 3: 499–503, (1993)). Controlled replication of adenoviral vectors, Whether through gene deletion or replication restricted to particular tissues, is of particular importance for in vivo applications involving adenovirus.

Replicative adenoviruses have been engineered to achieve selective targeting and amplification in vivo. Conditionally replicative and oncolytic adenoviruses have shown great promise in the treatment of cancer (Yu et al., *Curr. Opin. Mol. Ther.* 2002, Oct; 4(5):435–43, Bell et al., *Curr. Gene Ther.* 2002 May 2(2):243–54; Yoon et al. *Curr. Cancer Drug Targets* 2002 August; 1(2):85–107). Replicative adenoviruses can be delivered systemically, can be targeted to tumor cells, and can amplify their cytolytic effect in a tumor-specific manner, thereby providing substantial clinical benefit. See Henderson et al., U.S. Pat. No. 5,698,443; Hallenbeck et al., WO 96/17053. In such systems, a cell-specific transcriptional regulatory element controls the expression of a gene essential for viral replication, and thus, viral replication is limited to a cell population in which the element is functional. For example, an attenuated, replication-competent adenovirus has been generated by inserting the prostate-specific antigen (PSA) promoter and enhancer (PSE-TRE) upstream of the E1A transcription unit in adenovirus serotype 5 (Ad5), which virus demonstrates selective cytotoxicity toward PSA expressing cells in vitro and in vivo (Rodriguez et al. (1997) Cancer Res. 57:2559–2563).

Adenovirus of interest, including oncolytic adenovirus, conditionally replicative adenovirus, and replication defective adenovirus are frequently engineered to have genetic modifications in the E1 early gene region (genetic map units 1.30 to 9.24) of the virus genome. Typical modifications include deletions within the E1 gene region and/or replacement of the E1A promoter, introduction of a transgene, etc. Helper virus-independent production of adenovirus can require a packaging cell line that complements for viral gene products.

In order to produce recombinant adenoviral vectors for research and clinical trials, a packaging cell line is transfected with adenoviral E1 coding sequences. The cell line must express sufficient E1 gene products to supply in trans the E1A and E1B gene products that are required directly and indirectly for adenoviral DNA replication and virion production.

Although E1 complementation permits the production of recombinant adenoviral vectors, recombination events between the transfected E1 sequences in the host cell and the adenoviral vector can occur, resulting in the generation of replication competent adenovirus (RCA). This is especially problematic with large-scale production and successive propagation, and hence is problematic in the preparation of adenoviral particle stocks for therapeutic uses. Recombination and the development of RCA during recombinant adenoviral vector production not only contaminates viral stocks, but also is problematic relative to use of adenoviral vectors for in vivo applications. The problem of RCA generation has been known for some time, as described for example in Shenk et al., 1979, Cold Springs Harb. Symp. Quant. Biol. 44 (1979) 367–375 and Lochmuller, Human Gene Therapy, 1994, 1485–1491.

Available packaging cell lines typically contain adenoviral genes that have been deleted from the vector but are required for viral replication. In some cases overlapping sequences between the host cell and adenoviral vector are not completely eliminated. For example, the human embryonic kidney derived 293 cells (Graham et al. (1977) *J. General Virology* 36:59–74) have been widely used for propagating adenoviral vectors. However, due to substantial overlapping sequences between the adenoviral vector genome and the 293 cell line, recombination events occur that result in the generation of a replication competent adenoviral particles.

Improvements have been made to reduce the possibility of generating replication competent vectors due to recombination events between the packaging cell line and the vector via reduction in the sequences common to the vector and cell line (Fallaux et al. (1998) *Human Gene Therapy* 9:1909–1917). For example, U.S. Pat. No. 5,994,128 describes cell lines that complement for both E1A and/or E1B, while retaining the natural E1B promoter sequences. Studies performed using the PER.C6 cell line demonstrated that, despite a single region of homology between this cell line and the adenoviral vector, RCA were generated and cytopathic effects were observed in a cell based assay (Kim et al. (2001) *Exp. Mol. Med.* 33(3)145–9). When analyzed, the RCA were shown to contain the PGK promoter-E1 gene, derived from the plasmid that was employed to construct the PER.C6 cell line. The same problem of residual sequence overlap is true of other cell lines developed as alternatives to 293 cells. (See, for example, Massie et al., U.S. Pat. No. 5,891,690; Kovesdi et al., WO 95/34671, Kedan et al., PCT/US95/15947, Schiedner et al. (2002) *Human Gene Therapy*, 11:2105–2116). Consequently, there remains the potential for unwanted recombination events between the cell line and the adenoviral vector.

SUMMARY OF THE INVENTION

Adenovirus packaging cell lines are provided, wherein the cells comprise E1A and E1B coding sequences sufficient to complement deficiencies in adenoviral vectors and to allow growth of an E1 deficient adenovirus. The E1A and E1B sequences are operably linked to promoters that lack polynucleotide sequences sharing substantial sequence identity with native or wild type adenovirus E1A and E1B promoters. Such packaging cell lines reliably produce stocks of adenoviral particles with minimal potential for recombination event between the packaging cell line genome and the adenoviral vector. Viral stocks produced using the packaging lines of the invention are characterized by minimal or undetectable levels of RCA with maintenance of the intended recombination genotype.

In one embodiment of the invention, the packaging cell lines comprise stably integrated E1A and E1B expression vectors, where the E1A and E1B genes are operatively linked to a non-adenovirus heterologous promoter, which may be the same or different.

In another embodiment of the invention, methods for producing adenovirus substantially free of RCA are provided, wherein the adenovirus is grown in a cell line lacking polynucleotide sequences sharing substantial sequence identity with the adenovirus E1A and E1B promoters.

BRIEF DESCRIPTION OF THE DRAWINGS

FIGS. 4A and B depict the results of Southern blot analysis for E1A (FIG. 4A) and E1B (FIG. 4B) sequences of early and late passage cells from Clones 51 and 139. Asterisks indicate relevant bands.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., Molecular Cloning: A Laboratory Manual (Second Edition), Cold Spring Harbor Press, Plainview, N.Y., 1989 and Ausubel FM et al., Current Protocols in Molecular Biology, John Wiley & Sons, New York, N.Y. 1993, for definitions and terms of the art. It is to be understood that this invention is not limited to the particular methodology, protocols, and reagents described, as these may vary.

The publications and other materials including all patents, patent applications, publications (including published patent applications), and database accession numbers referred to in this specification are used herein to illuminate the background of the invention and in particular, cases to provide additional details respecting the practice. The publications and other materials including all patents, patent applications, publications (including published patent applications), and database accession numbers referred to in this specification are incorporated herein by reference to the same extent as if each were specifically and individually indicated to be incorporated by reference in its entirety.

An "adenovirus packaging cell" is a cell that is able to package adenoviral genomes or modified genomes to produce viral particles. It can provide a missing gene product or its equivalent. Thus, packaging cells can provide complementing functions for the genes deleted in an adenoviral genome and are able to package the adenoviral genomes into the adenovirus particle. The production of such particles requires that the genome be replicated and that those proteins necessary for assembling an infectious virus are produced. The particles also can require certain proteins necessary for the maturation of the viral particle. Such proteins can be provided by the vector or by the packaging cell. The packaging cell line is produced by genetically modifying a cell line permissive for adenovirus replication, to comprise adenovirus E1A and/or E1B coding sequences. In the adenovirus packaging cell lines of the present invention, adenovirus E1A and E1B coding sequences are operably linked to promoters that lack polynucleotide sequences sharing substantial sequence identity with native adenovirus E1A and E1B promoters.

A "host cell" includes an individual cell or cell culture which can be or has been a recipient of a viral vector(s) of the invention. Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with an adenoviral vector of this invention.

Figure 8:
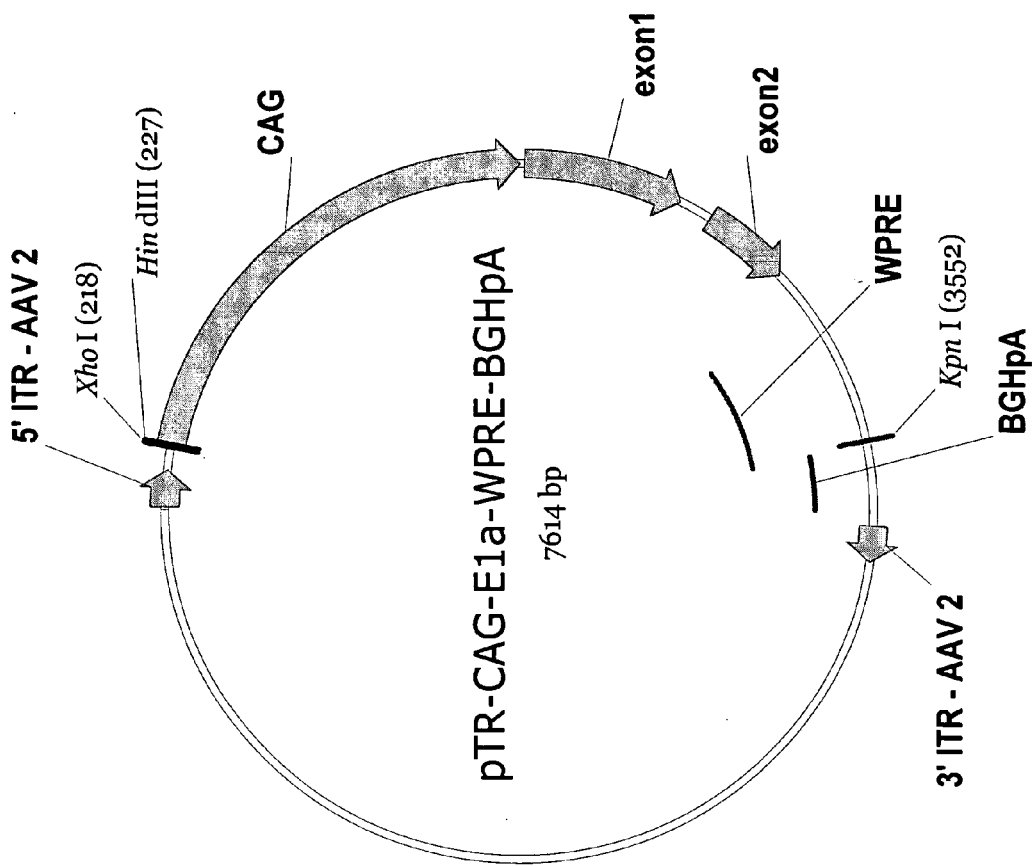
FIG. 8 illustrates an AAV-E1A expression cassette that is free from adenoviral E1A and E1B promoter sequences and includes in the 5' to 3' direction, a 5' ITR; a cytomegalovirus enhancer/chicken beta-actin/Rabbit β-globin promoter (CAG promoter; Niwa et al. (1991) Gene 108(2):193–9); exon 1 and exon 2 of E1A (SEQ ID NO:1); a woodchuck post-transcriptional regulatory element (WPRE); a bovine growth hormone poly A (BGHpA) sequence and a 3' ITR.
Figure 9:
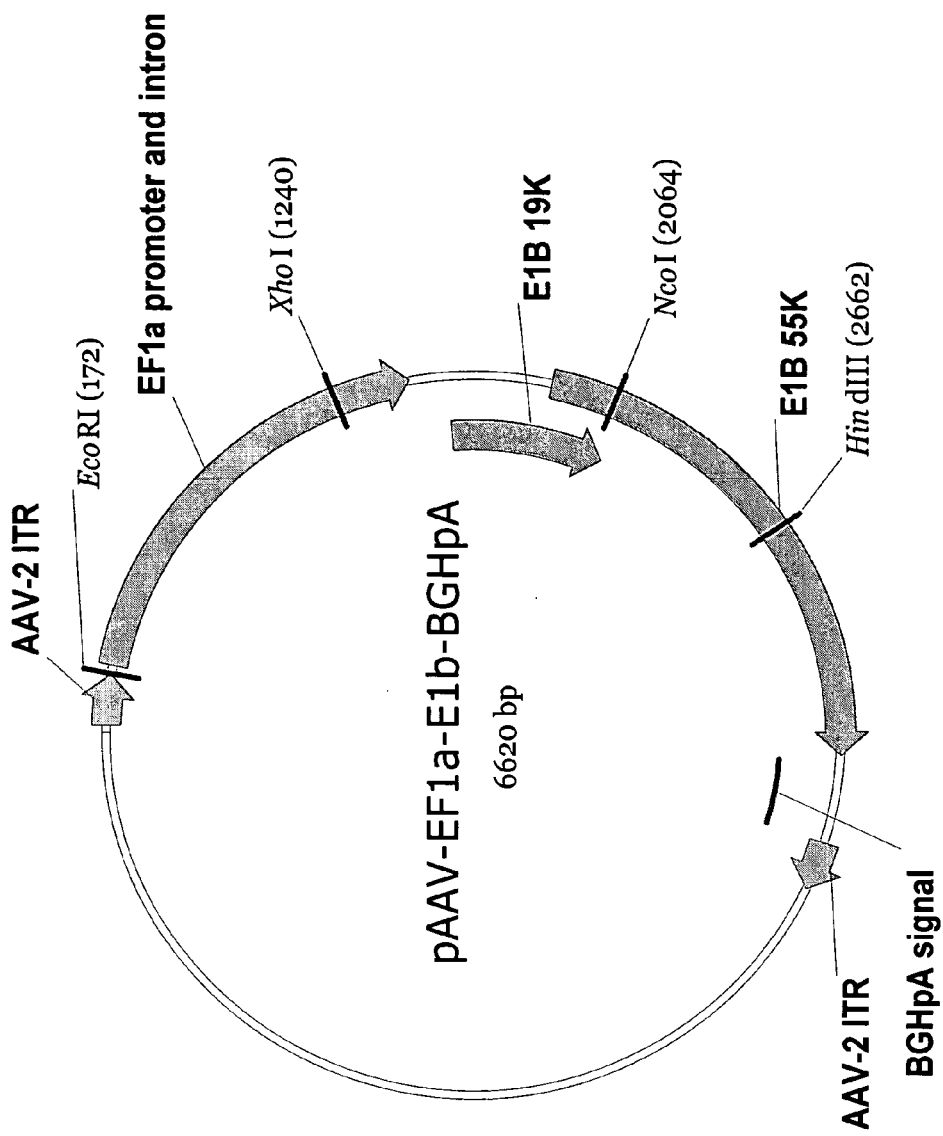
FIG. 9 illustrates an AAV-E1B expression cassette that is free from adenoviral E1A and E1B promoter sequences and includes in the 5' to 3' directions, a 5' ITR; an elongation factor 1-alpha promoter (EF1-alpha) promoter (Kim et al. (1990) Gene 91(2):217–23 and Guo et al. (1996) Gene Ther. 3(9):802–10) and enhancer; a 19K E1B coding sequence and a 55K E1B coding sequence (SEQ ID NO:4); a bovine growth hormone poly A (BGHpA) sequence and a 3' ITR.

The terms "adenovirus" and "adenoviral particle" as used herein include any and all viruses that may be categorized as an adenovirus, including any adenovirus that infects a human or an animal, including all groups, subgroups, and serotypes. Thus, as used herein, "adenovirus" and "adenovirus particle" refer to the virus itself or derivatives thereof and cover all serotypes and subtypes and both naturally occurring and recombinant forms. In one embodiment, such adenoviruses infect human cells. Such adenoviruses may be wildtype or may be modified in various ways known in the art or as disclosed herein. Such modifications include modifications to the adenovirus genome that is packaged in the particle in order to make an infectious virus. Such modifications include deletions known in the art, such as deletions in one or more of the E1a, E1b, E2a, E2b, E3, or E4 coding regions. Exemplary adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein. Exemplary AAV vectors for use in generation of E1A/E1B packaging lines are shown in FIGS. 8 and 9.

The term "replication defective" as used herein relative to an adenoviral vector means the viral vector cannot further replicate and package its genomes. For example, when the cells of a subject are infected with rAAV virions, the heterologous gene is expressed in the patient's cells, however, due to the fact that the patient's cells lack AAV REP and CAP genes and adenovirus accessory function genes, the rAAV is replication defective and wild-type AAV cannot be formed in the patient's cells.

As used herein, "packaging system" refers to a set of viral constructs comprising genes that encode viral proteins involved in packaging a recombinant virus. Typically, the constructs of the packaging system will ultimately be incorporated into a packaging cell.

The term "replication-competent" as used herein relative to an adenoviral vectors means the viral vectors and particles preferentially replicate in certain types of cells or tissues but to a lesser degree or not at all in other types. In one embodiment of the invention, the viral vector and/or particle selectively replicates in tumor cells and or abnormally proliferating tissue, such as solid tumors and other neoplasms. Such viruses may be referred to as "oncolytic viruses" or "oncolytic vectors" and may be considered to be "cytolytic" or "cytopathic" and to effect "selective cytolysis" of target cells. These include the viruses disclosed in U.S. Pat. Nos. 5,677,178, 5,698,443, 5,871,726, 5,801,029, 5,998,205, and 6,432,700.

The terms "virus", "viral particle", "vector particle", "viral vector particle", and "virion" are used interchangeably and are to be understood broadly as meaning infectious viral particles that are formed when, e.g., a viral vector of the invention is transduced into an appropriate cell or cell line for the generation of infectious particles. Viral particles according to the invention may be utilized for the purpose of transferring nucleic acids (e.g. DNA or RNA) into cells either in vitro or in vivo.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. Preferably, a vector of the invention comprises DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Nucleic acids are "operably linked" when placed into a functional relationship with another nucleic acid sequence. For example, a promoter or enhancer is operably linked to a coding sequence if it affects the transcription of the sequence. Generally, "operably linked" means that the DNA sequences being linked are contiguous. However, enhancers do not have to be contiguous Linking is accomplished by ligation at convenient restriction sites. If such sites do not exist, the synthetic oligonucleotide adapters or linkers are used in accordance with conventional practice.

The term "native" refers to a gene that is present in the genome of the wildtype virus or cell.

The term "naturally occurring" or "wildtype" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

The term "plasmid" as used herein refers to a DNA molecule that is capable of autonomous replication within a host cell, either extrachromosomally or as part of the host cell chromosome(s). The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeably with plasmids described herein.

The terms "administering" or "introducing", as used herein refer to delivery of an expression vector for stable integration of E1A and/or E1B coding sequences in a cell. A vector may be introduced into the cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage). As set forth above, the vector may be a plasmid, virus or other vehicle.

The term "recombinant" as used herein with reference to nucleic acid molecules refers to a combination of nucleic acid molecules that are joined together using recombinant DNA technology into a progeny nucleic acid molecule. As used herein with reference to viruses, cells, and organisms, the terms "recombinant," "transformed," and "transgenic" refer to a host virus, cell, or organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Recombinant viruses, cells, and organisms are understood to encompass not only the end product of a transformation process, but also recombinant progeny thereof. A "non-transformed," "non-transgenic," or "non-recombinant" host refers to a wildtype virus, cell, or organism that does not contain the heterologous nucleic acid molecule.

"Regulatory elements" are sequences involved in controlling the expression of a nucleotide sequence. Regulatory elements include promoters, enhancers, and termination signals. They also typically encompass sequences required for proper translation of the nucleotide sequence.

The term "promoter" refers to an untranslated DNA sequence usually located upstream of the coding region that contains the binding site for RNA polymerase II and initiates transcription of the DNA. The promoter region may also include other elements that act as regulators of gene expression. The term "minimal promoter" refers to a promoter element, particularly a TATA element that is inactive or has greatly reduced promoter activity in the absence of upstream activation elements.

The term "enhance" within the meaning of the invention may be any genetic element, e.g., a nucleotide sequence that increases transcription of a coding sequence operatively linked to a promoter to an extent greater than the transcription activation effected by the promoter itself when operatively linked to the coding sequence, i.e. it increases transcription from the promoter.

The phrase "hybridizing to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent wash conditions" in the context of nucleic acid hybridization experiments such as Southern and Northern hybridizations are sequence dependent, and are different under different environmental parameters. Longer sequences hybridize at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays" Elsevier, N.Y. Generally, highly stringent hybridization and wash conditions are selected to be about 5° C. to 20° C. (preferably 5° C.) lower than the thermal melting point (Tm) for the specific sequence at a defined ionic strength and pH. Typically, under highly stringent conditions a probe will hybridize to its target subsequence, but to no other sequences.

The terms "complement" and "complementary" refer to two nucleotide sequences that comprise antiparallel nucleotide sequences capable of pairing with one another upon formation of hydrogen bonds between the complementary base residues in the antiparallel nucleotide sequences.

The term "expression" refers to the transcription and/or translation of an endogenous gene, transgene or coding region in a cell.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson R J, Howell M T, Kaminski A (1990) Trends Biochem Sci 15(12):477–83) and Jackson R J and Kaminski, A. (1995) RNA 1(10):985–1000. The present invention encompasses the use of any IRES element, which is able to promote direct internal ribosome entry to the initiation codon of a cistron. "Under translational control of an IRES" as used herein means that translation is associated with the IRES and proceeds in a cap-independent manner. As used herein, the term "IRES" encompasses functional variations of IRES sequences as long as the variation is able to promote direct internal ribosome entry to the initiation codon of a cistron A "self-processing cleavage site" or "self-processing cleavage sequence" as referred to herein is a DNA or amino acid sequence, wherein upon translation, rapid intramolecular (cis) cleavage of a polypeptide comprising the self-processing cleavage site occurs to result in expression of discrete mature protein or polypeptide products. Such a "self-processing cleavage site", may also be referred to as a post-translational or co-translational processing cleavage site, e.g., a 2A site, sequence or domain. A 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly et al., J. Gen. Virol. 82:1027–1041, 2001). Constructs including the essential amino acid residues for expression of the cleavage activity by the FMDV 2A region have been designed (Ryan et al. (1991) J. Gen. Virol. 72:2727–2732; Furler et al. (2001) Gene Therapy 8: 864–873). 2A domains have also been characterized from aphthoviridea and cardioviridae of the picornavirus family (Donnelly et al. (1997) J. Gen. Virol. 78:13–21.

As used herein, the term "E1A" refers to all gene products of the adenovirus E1A region, including expression products of the two major RNAs: 13S and 12S. These are translated into polypeptides of 289 (SEQ ID NO:2) and 243 (SEQ ID NO:3) amino acids, respectively. These two proteins differ by 46 amino acids, which are spliced from the 12S mRNA, as described in Chow et al. (1980) Cold Spring Harb Symp Quant Biol. 44 Pt 1:401–14; and Chow et al. (1979) J. Mol. Biol. 134(2):265–303, herein specifically incorporated by reference. For the purposes of the invention, the packaging cell line may express the 289 polypeptide, the 243 polypeptide, or both the 289 and the 243 polypeptide. The term E1A is also used herein with reference to partial and variant E1A coding sequences.

As used herein, the term "E1B" refers to all gene products of the adenovirus E1B region, including the 3 major polypeptides, of 19 kd (SEQ ID NO:5) and 55 kd (SEQ ID NO:6). The E1B 19 kd and 55 kd proteins are important in cell transformation. For the purposes of the invention, the packaging cell line may express the 19 Kd polypeptide, the 55 Kd polypeptide, or both the 19 and the 55 Kd polypeptide. The term "adenovirus permissive" means that the adenovirus or adenoviral vector is able to complete the entire intracellular virus life cycle within the cellular environment. The cells may be derived from primary cell cultures, from established cell lines, and the like. Mammalian cells are preferred, including primate cells, e.g. human cells, monkey cells, etc. Although various primate cells are preferred and such human embryonic kidney cells are more preferred, any type of cell that is capable of supporting replication of the virus is acceptable in the practice of the invention. The term E1B is also used herein with reference to partial and variant E1B coding sequences.

"Replication" and "propagation" are used interchangeably and refer to the ability of an adenovirus vector to reproduce or proliferate. These terms are well understood in the art. For purposes of this invention, replication involves production of adenovirus proteins and is generally directed to reproduction of adenovirus. Replication can be measured using assays standard in the art and described herein, such as a virus yield assay, burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

Methods and Compositions of the Invention

The various methods and compositions are described below. Although particular methods are exemplified in the discussion below, it is understood that any of a number of alternative methods are applicable and suitable for use in practicing the invention. It will also be understood that an evaluation of the adenovirus vectors and methods of the invention may be carried out using procedures standard in the art, including the diagnostic and assessment methods described below.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

For techniques related to adenovirus, see, inter alia, Felgner and Ringold (1989) Nature 337:387–388; Berkner and Sharp (1983) Nucl. Acids Res. 11:6003–6020; Graham (1984) EMBO J. 3:2917–2922; Bett et al. (1993) J. Virology 67:5911–5921; Bett et al. (1994) Proc. Natl. Acad. Sci. USA 91:8802–8806.

Adenovirus Packaging Lines

Adenovirus packaging cell lines are provided, wherein the packaging cells provide adenovirus E1A and E1B sequences sufficient to complement and replicate an E1A/E1B deficient adenovirus, with minimal potential for generating wild type replication competent adenovirus (RCA). As used herein, RCA are replication competent adenovirus that do not require complementation by a packaging cell line for expression of E1A and/or E1B.

The packaging cell line comprises genetic sequences encoding human adenovirus E1A and E1B proteins. The genetic sequences may be native sequences or variants thereof. As used herein, substantial sequence identity refers to the level of sequence similarity that is sufficient for homologous recombination within the host cell. Candidate sequences can be empirically tested for recombination by, for example, testing two sequences for recombination during replication in the cell of interest. Typically, a sequence will lack substantial sequence identity if there is not more than about 20 nucleotides of contiguous, identical polynucleotide sequence, more usually not more than about 15 nucleotides of contiguous, identical polynucleotide sequence, and preferably not more than about 12 nucleotides of contiguous, identical polynucleotide sequence.

The reference sequence will usually be the adenovirus from which the vector is derived, e.g. human adenovirus 5; human adenovirus 2; etc. The lack of substantial sequence identity between the promoters driving expression of E1A and E1B in the packaging cell lines of the invention, and endogenous adenovirus E1A and E1B promoters, will minimize the possibility of recombination and resulting replication competent adenovirus (RCA) production.

For sequence, comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J. Mol. Biol. 215: 403–410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981).

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

The sequence of many adenovirus E1A and E1B proteins, e.g. from human adenovirus type 11; human adenovirus 41; human adenovirus 12; human adenovirus 5; human adenovirus 35; human adenovirus 41; human adenovirus 40; human adenovirus 4; human adenovirus 7; and human adenovirus 2 are known and publicly available. See, for example, the E1A polypeptide sequences, Genbank accession numbers AAN62486 (Ad 11), Q2AD5 (Ad 5); Q2AD2 (Ad2); and the E1B polypeptide sequences, Genbank Accession numbers. Q1AD25 (Ad5); and Q1AD22 (Ad2). The origin of the E1A and E1B coding sequences are most preferably from human Ad5. Other human and non-human adenoviral serotypes may also be used, including Ad2. The E1A and E1B sequences used in preparing the packaging lines of the present invention do not include the promoter sequences of either E1A or E1B. Usually the packaging line will not include adenovirus genetic sequences other than the E1A and E1B coding sequence.

Exemplary E1A and E1B coding sequences comprise two exon regions of E1A, which correspond to nucleotides 560–1545 of GenBank Accession No. M73260 or X02996 (presented herein as SEQ ID NO:1) and two E1B coding sequences that corresponds to nucleotides 1682–3825 of GenBank Accession No. M73260 or X02996 (presented herein as SEQ ID NO:4). It will be understood by one of skill in the art that the adenovirus sequences provided herein are merely examples of suitable sequences, as many adenovirus genomes have been characterized and are available for use. Exemplary E1A and E1B coding sequences for use in practicing the invention are provided in Table 1.

TABLE 1

Exemplary E1A and E1B Coding Sequences.

| SEQ ID NO | Name | Length | Type |
|---|---|---|---|
| 1 | E1A genomic sequence | 986 | DNA |
| 2 | E1A 289 | 289 | Protein |
| 3 | E1A 243 | 243 | Protein |
| 4 | E1B genomic sequence | 2144 | DNA |
| 5 | E1B19K | 176 | Protein |
| 6 | E1B 55K | 496 | Protein |
| 7 | E1A 289R cDNA | 873 | DNA |
| 8 | E1B 55K cDNA | 1491 | DNA |

The E1A and E1B sequences are operably linked to a non-adenoviral promoter. The promoter may be heterologous, where the term "heterologous" promoter is used herein to mean a promoter sequence that is not native to the packaging cell. Alternatively a homologous promoter is used, which is native to the packaging cell. For replication of adenovirus vectors comprising coding sequences for E1A and/or E1B, the promoter for E1A and/or E1B in the packaging cell line is preferably other than the promoter operably linked to E1A and/or E1B in the adenovirus vector.

In packaging cell lines of interest, the adenovirus E1A and E1B coding sequences are operably linked to a promoter that lacks polynucleotide sequences sharing substantial sequence identity with native adenovirus E1A and E1B promoters, such that homologous recombination is unlikely to take place. Such packaging cell lines reliably produce stocks of adenoviral particles free from recombination events between the packaging cell line genome and the replication defective adenoviral vector thereby minimizing the possibility of the generation of RCA.

In one embodiment of the invention, the packaging cell lines comprises stably integrated E1A and E1B expression vectors, where the E1A and E1B genes are operatively linked to a non-adenovirus promoter and have been introduced using separate expression vectors. The promoter may be a strong constitutive promoter of non-adenovirus origin. In one embodiment, the promoter operably linked to E1A is different than the promoter operably linked to E1B. In another embodiment, the promoter operably linked to E1A is the same as the promoter operably linked to E1B. The E1A and E1B genes may be coordinately expressed with such a promoter.

The E1A and E1B coding regions are preferably stably integrated in the packaging cell line genome. In a preferred embodiment, the site of E1A integration is physically separated from the site of E1B integration, e.g. on separate chromosomes, separate regions of the same chromosome, and the like.

In another embodiment of the invention, methods for producing adenovirus substantially free of RCA are provided, wherein the adenovirus is grown in a cell line lacking polynucleotide sequences sharing substantial sequence identity with the adenovirus E1A and E1B promoters.

Adenoviral vectors of interest for replication in the cell lines of the invention are deficient in expression of adenovirus genes essential for replication, particularly the adenoviral E1A and E1B genes. Such vectors are unable to produce sufficient viral proteins required for productive infection in the absence of exogenously provided viral genes. Adenoviral vectors deficient in expression of E1A and E1B may be deficient due to a variety of genetic changes, e.g. a lack of coding sequences for one or both of these genes; mutations in the coding sequences that render the polypeptide inoperable; alterations in promoter or enhancer sequences, and the like.

In some embodiments of the invention, the adenovirus vector is replication competent in a targeted cell type e.g. targeted tumor cells such as prostate cancer, liver cancer, etc., but in a non-targeted cell type the adenovirus is deficient in E1A and/or E1B expression. For example, the adenovirus vector may comprise adenoviral genes essential for replication that are operably linked to a transcriptional regulatory element that is cell type specific, cell state specific, etc. Such vectors benefit from growth in a packaging cell line such as described herein, e.g., to generate large numbers of virus particles in vitro.

The promoter sequences used to express E1A and E1B may be identical or non-identical. Where the promoter sequences are identical, the E1A and E1B coding sequences may be coordinately expressed, e.g. where both coding sequences are operatively linked to a single promoter and an IRES is present between the two coding sequences.

In one embodiment of the present invention, one or both promoters are regulatable promoters, e.g., promoters inducible with an agent, such as metals or hormones (Brinster et al. *Nature* (1982), 296, 39–42), or hormones (Lee et al. *P.N.A.S. USA* (1988), 85, 1204–1208; (1981), 294, 228–232; Klock et al. *Nature* (1987), 329, 734–736; Israel and Kaufman, *Nucleic Acids Res.* (1989), 17, 2589–2604).

Alternatively, in yet another embodiment, the promoter is a constitutive promoter. Promoters can be obtained from the genomes of viruses such as polyoma virus, fowlpox virus, bovine papilloma virus, avian sarcoma virus, cytomegalovirus, a retrovirus, hepatitis-B virus and Simian Virus 40

(SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

In one exemplary, embodiment the LTR of MMLV is operatively linked to the E1A gene in a first retroviral expression vector and in a second retroviral expression vector, the LTR of MMLV is operatively linked to and used to direct the expression of, the E1B gene. In another exemplary embodiment, the CAG promoter is operatively linked to exon 1 and exon 2 of the E1A gene (SEQ ID NO:1) in a first expression vector and in a second expression vector, the EF1-alpha promoter is used to direct the expression of a 19k and a 55k E1B coding sequence (SEQ ID NO:4).

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation, and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, etc. The enhancer may be spliced into the expression vector at a position 5' or 3' to the coding sequence, but is preferably located at a site 5' from the promoter.

Generation of Cell Lines for Packaging Adenovirus

Site-specific DNA cleavage is performed by treating plasmid or other DNA with the suitable restriction enzyme (or enzymes) under conditions which are generally understood in the art, and the particulars of which are specified by the manufacturer of these commercially available restriction enzymes. (See, e.g. New England Biolabs, Product Catalog.) In general, about 1 μg of plasmid or other DNA is cleaved by one unit of enzyme in about 20 μl of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499–560 (1980). (See also, Sambrook and Russell, supra.)

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° C. in 50 mM Tris (pH 7.6) 50 mM NaCl, 6 mM $MgCl_2$, 6 mM DTT and 5–10 μM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 μl volumes under the following standard conditions and temperatures: 20 mM Tris-Cl pH 7.5, 10 mM $MgCl_2$, 10 mM DTT, 33 mg/ml BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 mM total end concentration). Intermolecular blunt end ligations (usually employing a 10–30 fold molar excess of linkers) are performed at 1 μM total ends concentration.

A vector comprising E1A or E1B is introduced into a permissive host cell. Many such vectors are available, including plasmid vectors, viral vectors, etc. The vector components may include, but are not limited to, one or more of the following: an origin of replication, one or more marker genes, an enhancer element, a promoter, and a transcription termination sequence.

Preferred expression vectors for the introduction of E1A/E1B coding sequences are those capable of stable integration in a host cell that are maintained at high frequency in daughter cells. In one preferred embodiment the expression vectors are of viral origin. Several recombinant viral vectors find utility in effective delivery of E1A/E1B coding sequences into cells in order to produce a packaging cell line according to the present invention including for example, retroviral vectors, lenitviral vectors, adenovirus-associated vectors (AAV), herpes virus vectors, pox virus vectors and the like. In another preferred embodiment, the expression vector is a plasmid derived from a retrovirus. In another embodiment, the expression vector is a plasmid derived from a lentivirus. Hybrid vectors may also be used, which contain sequences from a retrovirus and a second non-Ad virus. In a further preferred embodiment, the expression vector is a retroviral vector derived from Moloney Murine Leukemia Virus (MMLV), which has a cloning capacity of at least 7.5 kilobases. Non-viral expression vectors may alternatively be used so long as they contain genetic elements that facilitate integration into the host cell genome.

Expression vectors comprising the coding sequence for E1A and/or E1B polypeptide production are introduced into appropriate cell lines for large scale adenoviral vector production using the methodology appropriate to the particular vector/cell line combination in order to obtain cells which have the E1A and/or E1B coding sequence stably integrated in their genome. Stable transfection is demonstrated by the establishment of cell lines or clones comprised of a population of daughter cells containing the transfected DNA stably integrated into their genomes.

The introduction of viral and non-viral vectors into cells is carried out using standard techniques routinely employed by those of skill in the art. Expression vectors of the present invention may additionally contain non-coding and coding sequences, including those imparting selectable traits to the cell line.

Expression vectors comprising a coding sequence for E1A and/or E1B may be introduced into cells sequentially or simultaneously using standard transfection methods (Sambrook, supra), or in the most preferred embodiment, packaged into infectious viral particles and introduced into the cell line via transduction. As would be readily understood, the term "introduced" embraces any methodology employed to deliver DNA sequences into a cell, including transduction and transfection methods as appropriate to the expression vector (e.g., infectious particles versus DNA plasmids). Using separate expression vectors for E1A and E1B, respectively, introduced sequentially or simultaneously, further reduces potential recombination events between the packaging cell genome and an Ad vector, as each integrates into the packaging cell genome in a different location. The invention provides the advantage of spatial separation of the expression vectors within the genome, providing for the further decrease in recombination events that could generate RCA or a loss of tissue specific replication.

Replication defective and/or replication competent adenoviral vectors produced using the packaging cell lines of the invention are substantially free of RCA. Substantially free of RCA means that the amount of RCA is sufficiently low such that no toxicity results from in vivo administration of adenoviral vectors produced using the packaging cell lines of the invention. Preferably, an adenovirus vector preparation that is substantially free of RCA contains from about zero to about 1 in about $10^4$ RCA particles per patient dose, where a typical patient dose is about $10^{12}$ to about $10^{13}$ viral particles. However, by way of example, a patient dose of $10^{13}$ total viral particles may contain from zero to 10, $10^2$, $10^3$, $10^4$, $10^5$, $10^6$, $10^7$ or $5 \times 10^7$ recombinant viral particles and be considered to be substantially free of RCA, so long as no toxicity results following in vivo administration.

Cell Lines

Expression vectors comprising the coding sequence for E1A and/or E1B polypeptide production are introduced into appropriate cell lines for large scale adenoviral vector production. The cell line is then cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan. Exemplary host cells that may be used to make a packaging cell line according to the present invention include, but are not limited to A549, HeLa, MRC5, W138, CHO cells, Vero cells, human embryonic retinal cells, or any eukaryotic cells, as long as the host cells are permissive for growth of adenovirus. Some preferred host cell lines include human tumor cell lines. In a preferred embodiment, the packaging cell line is derived from PC-3 cells (ATCC number CRL-1435). PC-3 cells were initiated from a metastatic prostate cell adenocarcinoma. PC-3 cells are particularly advantageous for the large-scale production of clinical grade Ad vectors as they can be adapted for passage in serum free media. Other cell types include, but are not limited to, cells derived from primary cell cultures, e.g., human primary prostate cells, human embryonic retinal cells, human stem cells. Eukaryotic dipoloid and aneuploid cell lines are included within the scope of the invention.

Preferred cell lines are adaptable to serum free medium.

A candidate cell line may be tested for its ability to support adenovirus replication by methods known in the art, e.g. by contacting a layer of uninfected cells, or cells infected with one or more helper viruses, with virus particles, followed by incubation of the cells. The formation of viral plaques, or cell free areas in the cell layer, is the result of cell lysis caused by the expression of certain viral products. Cell lysis is indicative of viral replication.

Adenoviral Serotypes

A packaging cell line according to the present invention is useful for the large-scale production of clinical grade Ad vectors derived from any known adenovirus serotype, as well as chimeric adenoviruses comprised of sequences derived from more than one serotype. The present invention contemplates the use of Ad vectors from all adenoviral serotypes. Adenovirus serotypes 1 through 47 are currently available from American Type Culture Collection (ATCC, Manassas, Va.), and the invention finds utility in production of any other serotype of adenovirus available from any source, so long as the packaging cell line of the invention is capable of replicating the virus. The adenoviruses that can be produced using a packaging line according to the invention may be of human or non-human origin. For instance, an adenovirus can be of subgroup A (e.g., serotypes 12, 18, 31), subgroup B (e.g., serotypes 3, 7, 11, 14, 16, 21, 34, 35), subgroup C (e.g., serotypes 1, 2, 5, 6), subgroup D (e.g., serotypes 8, 9, 10, 13, 15, 17, 19, 20, 22–30, 32, 33, 36–39, 42–47), subgroup E (serotype 4), subgroup F (serotype 40, 41), or any other adenoviral serotype.

Recombinant adenoviruses produced using the packaging lines of the invention may include deletion or other genetic modification in addition to deficiencies in E1A and/or E1B coding regions. Recombinant adenoviruses useful in this invention may optionally bear other genetic changes, e.g. inclusion of a transgene, and the like.

In one embodiment, the packaging cell line is both permissive for adenovirus replication, and adenovirus infection. The primary receptor of adenovirus serotypes 2 and 5 has been identified and named CAR (Coxsackievirus and Adenovirus Receptor; GenBank Accession no. HSU90716) by Bergelson et al. (1997) Science 275:1320, and shown to be a receptor for all adenovirus subgroups except subgroup B by Roelvink et al. (1998).

In another embodiment the packaging lines on the invention find utility in production of adenoviral vectors that comprise a targeting ligand included in a capsid protein of the particle, such as a modified fiber protein comprising a ligand or single chain antibody in the HI loop or carboxyl-end (C-terminus) of the fiber protein or in protein IX. Adenoviral vectors that comprise a targeting ligand are described for example in WO 00/67576, WO 99/39734, U.S. Pat. Nos. 6,683,170, 6,555,368, 5,922,315, 5,543,328 and 5,846,782. In yet another embodiment, the packaging lines on the invention find utility in production of adenoviral vectors that include other mutations to the fiber protein, such as those exemplified in U.S. application Ser. No. 10/403, 337, WO 98/07877, WO 01/92299, and U.S. Pat. Nos. 5,962,311, 6,153,435, 6,455,314, 5,731,190, 6,057,155, 5,543,328, 5,756,086, 6,127,525, 5,922,315 and Wu et al. (J. Virol. 2003 Jul. 1;77(13):7225–7235).

Pharmaceutical Compositions

Adenovirus vectors produced using the packaging lines of the invention may be formulated for use, e.g. in clinical applications. The eluant is optionally concentrated and diafiltered by conventional methods, e.g. with a hollow fiber concentrator. In a final preparation for use, the virus sample may be sterile filtered. A variety of filters suitable for this purpose are known in the art, e.g. nitrocellulose membrane filters; cellulose acetate membrane filters; PVDF (modified polyvinylidene fluoride) membrane filters; and the like. Preferred are PVDF membrane filters (for example Millipore Millipak filters).

The sterile filtered virus suspension is formulated for use in vitro or in vivo. Aqueous compositions comprise an effective amount of the virus, suspended in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Formulations include injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions; saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical composition are adjusted according to well-known parameters.

Formulations may be optimized for the desired storage conditions. In one embodiment of the invention, particularly with virus formulated for clinical use, the samples are stored in liquid form, preferably at cool temperatures, usually less than about 10° C., more usually less than about 5° C. For such conditions, a preferred medium for storage comprises 5% sucrose, 1% glycine, 1 mM $MgCl_2$, 10 mM Tris, and small amounts of a surfactant. One surfactant of interest is a non-ionic detergent, e.g. Tween 80, Tween 20, etc., at a concentration of from about 0.01% to about 0.1%, preferably about 0.05%. Other surfactants of interest include poloxamer block polymers of polyethylene glycol polypropylene glycol such as Lutrol F-68, Lutrol F-127, etc., e.g. at a concentration of from about 5% to about 10%, preferably about 8%.

For samples that are stored frozen, for example at −20° C. or −80° C., suitable buffers are as described above, however the inclusion of surfactants is generally less important to stability, and may be omitted. Glycerol at a concentration of from about 2% to about 10% may be included.

The viral particles of the present invention may include classic pharmaceutical preparations for use in therapeutic regimens, including their administration to humans. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, injection to a resected tumor bed, regional (i.e., lymphatic) or general administration is contemplated. It also may be desired to perform continuous perfusion over hours or days via a catheter to a disease site, e.g., a tumor or tumor site.

An effective amount of the adenovirus vector may be administered to a patient as a composition in a pharmaceutically acceptable excipient (and may or may not be in the same compositions), including, but not limited to, saline solutions, suitable buffers, preservatives, stabilizers, and may be administered in conjunction with suitable agents such as antiemetics. An effective amount is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state. Some individuals are refractory to these treatments, and it is understood that the methods encompass administration to these individuals. The amount to be given will be determined by the condition of the individual, the extent of disease, the route of administration, how many doses will be administered, and the desired objective.

An effective amount of the therapeutic agent is determined based on the intended goal, for example (i) inhibition of tumor cell proliferation, (ii) elimination or killing of tumor cells, (iii) vaccination, and the like. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired.

Assessment of the efficacy of a particular treatment regimen may be determined by any of the techniques known in the art, including diagnostic methods such as imaging techniques, analysis of serum tumor markers, biopsy, and/or an evaluation of the presence, absence or amelioration of tumor associated symptoms. It will be understood that a given treatment regime may be modified, as appropriate, to maximize efficacy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

EXAMPLE 1

Construction of E1A/E1B Packaging Cell Lines

Construction of MMLV Expression Vectors. Moloney Murine Leukemia Virus (MMLV)-derived plasmids were utilized for constructing an E1A retroviral expression vector and an E1B retroviral expression vector. Specifically, the pRT43.2F3 plasmid was utilized. The construction of pRT43.2F3 is summarized below and is completely described in U.S. Pat. No. 5,686,279.

pRT43.2F3. This retroviral vector contains modified 5' LTRs that direct efficient transcription in the cell type where retrovirus is to be produced. The retroviral vectors of the invention are modeled after pZen (Johnson et al., *EMBO Journal* 8(2):441–448 (1989)), a neo-version of pZIP-neoSVX (Cepko et al., *Cell* 37:1053–1062(1985)), in which the gene product to be expressed is cloned downstream of the splice acceptor in the position normally occupied by the neo cassette (Cepko et al., supra). In addition, viral gag sequences up to the Nar I site of MMLV (nucleotide 1038) were added for improved packaging (Armentano et al., *J. Virol.* 61:11647–1650 (1987)) and the Xho I to Cla I fragment of pZIPneoSVX was deleted (Cepko et al., supra). The Eco RI to Apa I polylinker from pIK1.1 was inserted downstream of the splice acceptor to enable transfer of inserts from pIK plasmids into retroviral constructs. The resulting plasmid is designated pRTD1.2 and contains both 5' and 3' MMLV LTRs. The 5' LTR U3 region of pZIP-neoSVX was replaced with the MMSV U3, derived from the HindIII/Sac I fragment of pIKMMSV, to generate pRTD4.2.

In pRTD2.2, the U3 region of the 5' LTR of pZIPneoSVX was replaced with the Hind III/Sac I fragment from pIK1.1 encoding the CMV immediate early enhancer/promoter, which was fused to the MMLV R region by an oligonucleotide that encodes nucleotides 19 (Sac I) to +1 of the HCMV promoter linked to nucleotides +1 to +32(KpnI) of MMLV (Schinnick et al., *Nature* 293:543–548 (1980)).

pRTD2.2SVG was constructed by replacement of the (750 bp) Sac I to Bst EII fragment of pRTD2.2 with the (736 bp) Sac I to Bst EII fragment of LXSN (Miller and Rosman, *BioTechniques* 7:980–990 (1989)). pRTD2.2SSA was constructed by replacement of the (1441 bp) Sac I to Eco RI fragment of pRTD2.2 with the (1053 bp) Sac I to Eco RI fragment of LXSN (Miller and Rosman, supra). pRTD2.2SVGE- was constructed by synthesis of an oligonucleotide encoding nucleotides 2878–2955 of pLXSN (GenBank Accession Bank, M28248) which had been appended by addition of an Apa I site on it's 5' end. This was used to replace the Apa I to Nhe I fragment of pRTD2.2SVG, which contains the DNA sequence 3' of the of the polylinker and 5' of the Nhe I site in the 3' LTR. These retroviral vector constructs of the invention have a pBR322 backbone and include pRTD2.2, pRTD4.2, pRTD2.2SVG, pRTD2.2SVGE- and pRTD2.2SSA.

In order to permit plasmid replication in cells which express the SV40 T antigen, the sequences between the 5' and 3' LTRs of pRTD2.2 were cloned between the SacI and Eco RI sites of pIK1.1, described above, which contains the SV40 origin of replication to form vector pIKT2.2. pIKT2.2SVG was constructed by insertion of the fragment defined at its 5' end by the Sac I site in the HCMV promoter of pRTD2.2SVG and defined at its 3' end by an Eco RI site located 750 bp downstream of the 3' LTR of pRTD2.2SVG, between the SacI and Eco RI sites of pIK1.1. pIKT2.2SVGE-F3 was constructed by replacing the 182 base pair ApaI to NheI fragment of pIKT2.2SVGF3 with the 80 base pair ApaI to NheI fragment from pRTD2.2SVGE-F3 as described above.

pRT43.2F3 was derived from pIKT2.2SVGE-F3 by replacing the Eco RI to ApaI polylinker located approximately 750 base pairs downstream from the 3' LTR with a synthetic oligonucleotide containing an AscI recognition site. In addition, the Nde I site at the 3' end of the viral gag sequences has been converted to an XhoI site by oligonucleotide insertion. pRT43.3PGKF3 was derived from pRT43.2F3 first by removal of the 3' LTR in pRT43.2F3 and insertion of a 3' LTR in which the sequences from PvuII to XbaI were deleted (MMLV, GenBank session #J02255 nucleotide numbers 7938–8115). In addition the MMLV splice acceptor region has been replaced with the human phosphoglycerate kinase gene promoter (GenBank session #M11958 nucleotides 2–516), which was cloned into a polylinker with a XhoI site-at its 5' end and an Eco RI at its 3' end.

Figure 1:
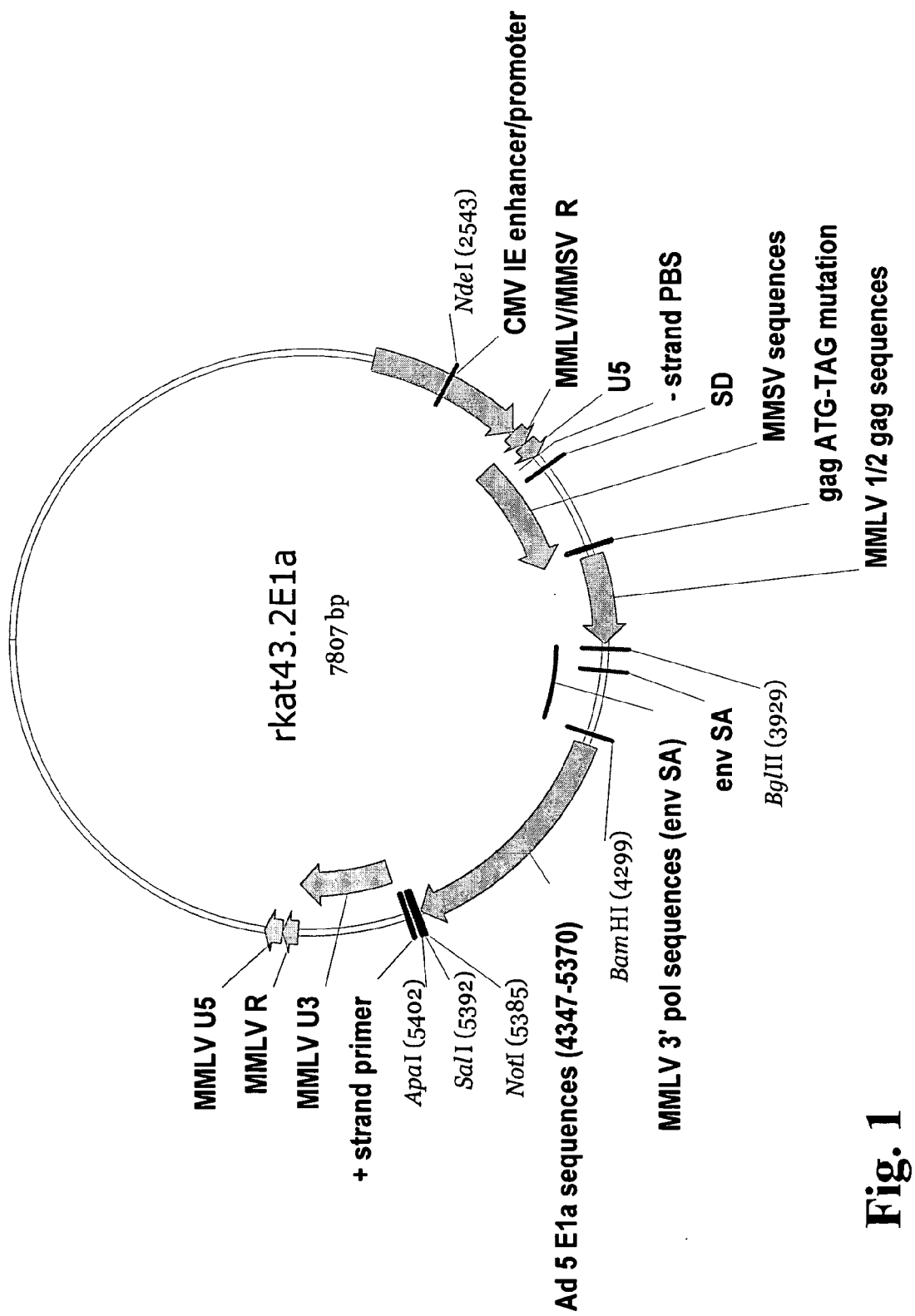
FIG. 1 illustrates an MMLV-E1A retroviral expression cassette that is free from adenoviral E1A and E1B promoter sequences.

E1A Expression Vector—rkat 43.2E1A. rkat 43.2E1a (FIG. 1) is a retroviral vector that expresses the Ad5 E1A open reading frame under the control of the retroviral LTR. Thus, neither an adenoviral nor mammalian host cell derived promoter is utilized for directing expression of Ad E1A. rkat 43.2E1A was generated by replacing the CD4/ζ coding sequences of pRT43.2F3 (U.S. Pat. No. 5,686,279 and Roberts et al., *J. Immunology* (1998) 161:375–384) with the DNA sequences coding for Ad5 E1A open reading frames (Ad5 nucleotides 548–1575, Genbank Accession X02992: SEQ ID NO:1).

Figure 2:
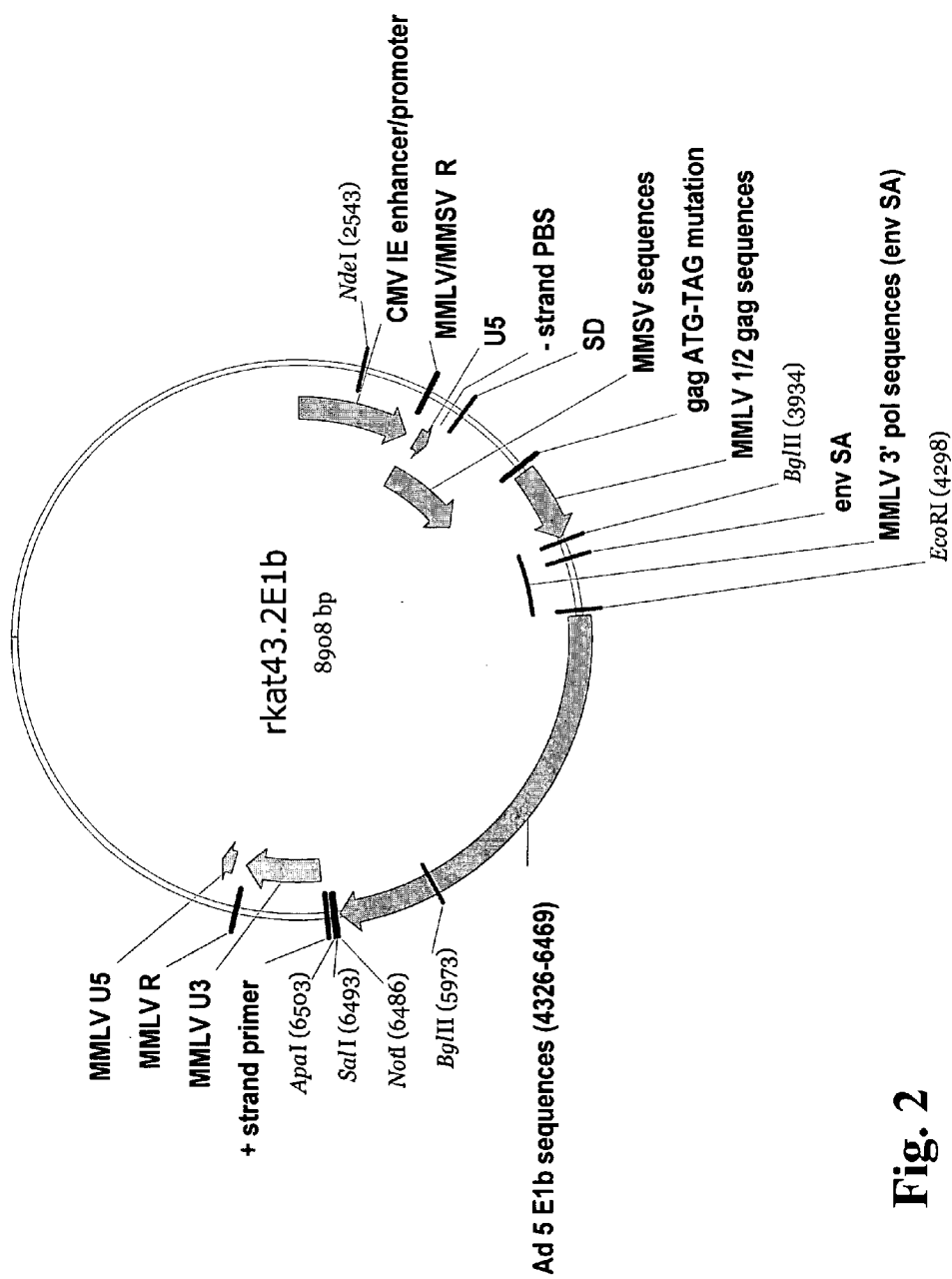
FIG. 2 illustrates an MMLV-E1B retroviral expression cassette that is free from adenoviral E1A and E1B promoter sequences.

E1B Expression Vector—rkat 43.2E1B. rkat 43.2E1B (FIG. 2) was similarly generated from pRT43.2F3. This vector expresses the Ad5 E1B open reading frames (nucleotides 1682–3825 of Ad5, Genbank Accession X02996: SEQ ID NO:4) under the control of the retroviral LTR and does not include an adenoviral or mammalian host cell derived promoter. rkat 43.2E1A was generated by replacing the CD4/ζ coding sequences of pRT43.2F3 (U.S. Pat. No. 5,686,279 and Roberts et al., supra) with the cDNA sequences coding for Ad5 E1B mRNA.

Transient Retrovirus Production. Infectious particles comprising the E1A and E1B expression vectors were produced using standard methodology. Transient viral supernatants were prepared by co-transfecting the rkat 43.2E1A or rkat 43.2E1B plasmid with MCVecog/p and 6.1CMVamphoenv. The resulting viral supernatants MMLV-E1A (designated C5.03-0.04) and MMLV-E1B (designated C5.05-0.06) were then utilized for cell transduction.

A549 Cell Transduction. Naive A549 cells (ATCC No. CCL-185) were cultured in complete medium including DMEM/High, 10% fetal bovine serum, 1% glutamine and 1% Pen-Strep. Adenoviral E1A and E1B coding sequences were stably introduced into A549cells by co-infecting the cells with MMLV-E1A and MMLV-E1B viruses by spinoculation. $1.5 \times 10^5$ cells were resuspended in 1 ml of E1A/E1B viral supernatants and 8 µl/ml of polybrene. The cell and virus mixture was then centrifuged at 3400 rpm at 34° C. for 4 hours. To ensure optimal E1A/E1B ratios, three different E1A/E1B viral ratios (25% E1A/75% E1B, 50% E1A/50% E1B, 75% E1A/25% E1B) were used in spinoculation. MMLV-green fluorescent protein (GFP) virus was included as a control for monitoring viral transduction efficiency. After spinoculation, the three populations were resuspended with complete medium, transferred into 6-well plates and incubated in 5% incubator at 37° C. for 8 days.

Dilutional Cloning of E1A/E1B Transduced Cells. The three populations were dilution cloned on 10-cm dishes. After 18 days in culture, there were clear differences between the three populations. Clones from all three populations were picked into 96-well plates. Each plate was then trypsinized and split into two 96-well plates so that one could be used for a functional screen and the other for retrieval of functional clones, once identified. The cells were grown for 5 days to allow for expansion.

Functional Screening for E1 Complementation. An E1-deficient recombinant adenovirus carrying a GFP transgene was used to test each of the E1A/E1B transduced clones for the ability to support adenoviral replication. One set of the duplicated 96-well plates containing candidate clones was infected with the E1-deficient Ad-GFP virus at an M.O.I. of 10 at 100 µl/well for 48 hours. The cells were subjected to 3 freeze/thaw cycles to release viral particles. These lysates were used to infect HuH7 cells. Three days after infection, the HuH7 cells were harvested and analyzed by FACS to evaluate for GFP expression. Table 2 shows the results of functional characterization of a number of clones with respect to GFP expression. This functional characterization is based on infection of HuH7 cells with adeno-GFP supernatants from candidate clones and evaluation of amplification as the initial screen. The clones whose supernatants exhibited high GFP expression in HuH7 cells were considered to be candidate E1A/E1B-positive packaging clones. Those clones that transduced the HuH7 cells to the greatest extent were expanded and titered in plaque assays, as further described below.

TABLE 2

Functional Screen of E1A/E1B complementing clones.

| Clones | Functional Screen |
|---|---|
| A549 | 5.50% |
| Cl. 51 (50/50) | 91% |
| Cl. 54 (50/50) | 64.50% |
| Cl. 58 (50/50) | 66.80% |
| Cl. 100 (50/50) | 49.30% |
| Cl. 110 (50/50) | 61.90% |
| Cl. 122 (50/50) | 68.40% |

TABLE 2-continued

Functional Screen of E1A/E1B complementing clones.

| Clones | Functional Screen |
|---|---|
| Cl. 125 (50/50) | 54.70% |
| Cl. 139 (50/50) | 77.60% |
| Cl. 143 (50/50) | 65.90% |
| Cl. 40 (50/50) | 46% |
| Cl. 3 (25/75) | 61% |
| Cl. 9 (25/75) | 68.40% |
| Cl. 4 (25/75) | 54.40% |
| Cl. 33 (25/75) | 80.40% |
| Cl. 41 (25/75) | 69% |
| Cl. 42 (25/75) | 53% |
| 293 AAV | 99% |

The cell population derived following spinoculation with an E1A/E1B viral ratio of 50% E1A/50% E1B had the fewest number of surviving "healthy" clones (as determined by morphology), prior to infection with E1 Ad-GFP, but produced a higher proportion of clones capable of complementing E1 deficient viruses. The clones arising from the 75% E1A/25% E1B transduction ratio exhibited the best overall growth characteristics, but did not yield the same observed complementation of the E1 deficient virus of the 50%-E1A 50%-E1B clones.

Evaluation of clones for ability to complement E1-deleted and oncolytic adenovirus: E1A/E1B complementing cells were evaluated as candidate packaging cells, by infection with an E1A deleted GFP-expressing replication defective adenovirus in a virus yield assay in which E1A/E1B complementing cells, parental and E1A/E1B-negative cells were compared. By comparing virus production from each clone, the E1A/E1B complementing cells are evaluated quantitatively for their ability to support viral replication. The test clones were infected with the E1 deleted GFP-expressing replication defective adenovirus at an M.O.I of 5 for 4 hrs, refed with fresh media and incubated for 72 hr. Cells and media were harvested together, and subjected to 3 rounds of freeze/thaw. Serial dilutions were done in serum-free media and assayed on 293 cells which had been plated 24 hr earlier on $0.5 \times 10^6$ cells/well/4 ml media on 6-well plates. Incubate for 3–4 hrs. The samples were aspirated and 4 ml agarose (0.8% agarose in complete medium) applied as an overlay to each well. The plates were left at room temperature to solidify and incubate for plaque development. Table 3 shows the titers obtained by plaque assay. The best clones were then analyzed in a further plaque assay using a replication competent (oncolytic) adenoviral vector, AFP-CG8900 (Table 2B). On the basis of these results, 2 clones, designated E1A/E1B Clone 51 and Clone 139, respectively, were further characterized.

TABLE 3

Ability of E1A/E1B Complementing Clones To Support Viral Replication.

| Clones | A. Ad-GFP infection Titers (pfu) × 1e5/ml | B. AFP-CG8900 infection Titers (pfu) × 1e8/ml |
|---|---|---|
| A549 | 0.0 | 1.0 |
| Cl. 51 (50/50) | 6.0 | 3.0 |
| Cl. 54 (50/50) | 4.0 | 1.0 |
| Cl. 58 (50/50) | 7.5 | 1.0 |
| Cl. 100 (50/50) | 1.0 | |

TABLE 3-continued

Ability of E1A/E1B Complementing Clones
To Support Viral Replication.

| Clones | A. Ad-GFP infection Titers (pfu) × 1e5/ml | B. AFP-CG8900 infection Titers (pfu) × 1e8/ml |
|---|---|---|
| Cl. 110 (50/50) | 6.0 | 1.0 |
| Cl. 122 (50/50) | 2.0 | |
| Cl. 125 (50/50) | 2.8 | |
| Cl. 139 (50/50) | 3.7 | 3.0 |
| Cl. 143 (50/50) | 4.0 | |
| Cl. 40 (50/50) | 0.0 | |
| Cl. 3 (25/75) | 1.0 | |
| Cl. 9 (25/75) | 0.2 | |
| Cl. 4 (25/75) | 0.0 | |
| Cl. 33 (25/75) | 0.7 | 0.3 |
| Cl. 41 (25/75) | 1.0 | |
| Cl. 42 (25/75) | 0.0 | |
| 293 AAV | 2 × 10e7 | 3.0 |

Figure 3:
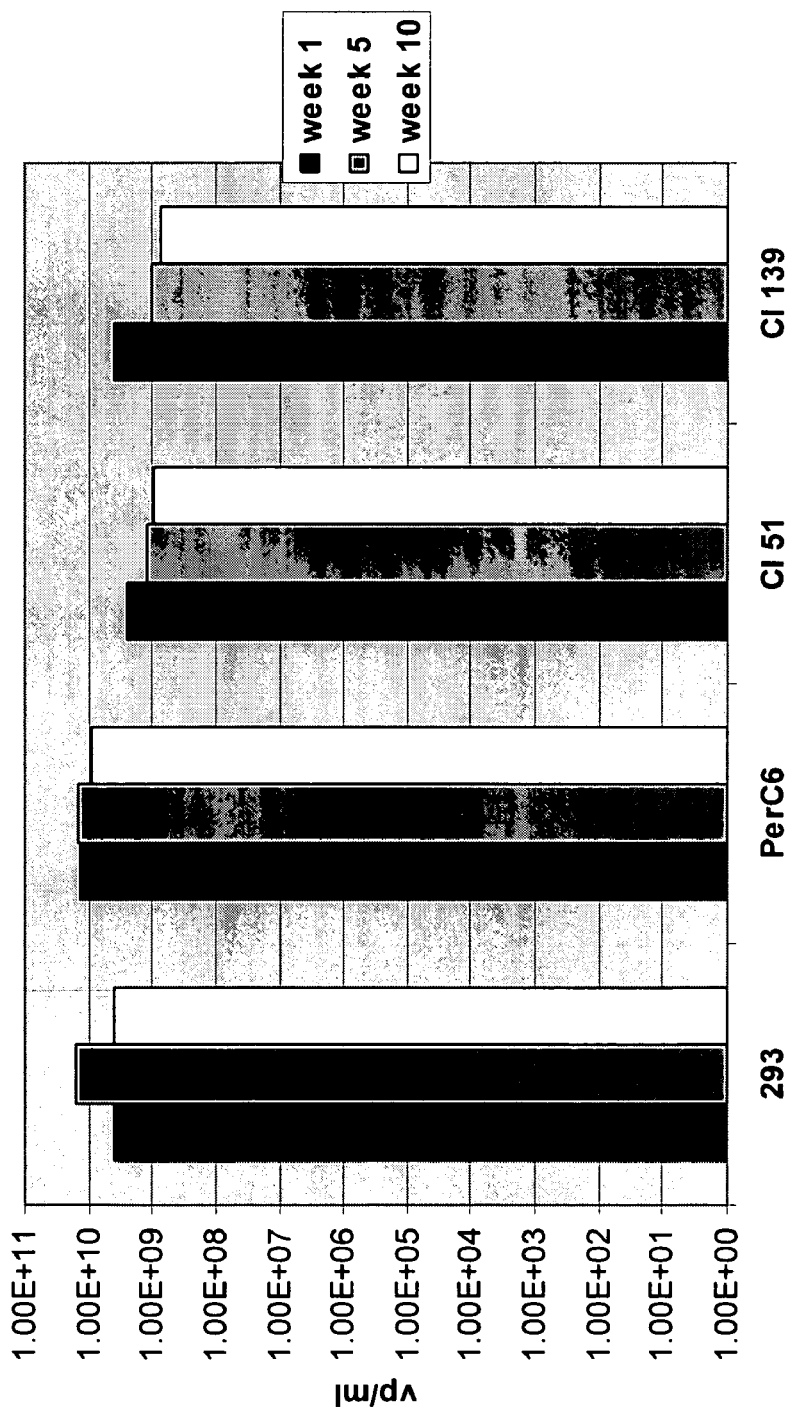
FIG. 3 illustrates the production of replication defective adenovirus which expresses GM-CSF on 293, PerC6, Clone 51 and Clone 139 cells.

Production of E1-deleted Adenovirus and Stability of E1 Clones 51 and 139. 293 cells, PerC6 cells, and cells derived from E1A/E1B Clones 51 and 139 were grown and infected with E1-deleted Adeno-GMCSF at an MOI=75. After 72 hours, cells were harvested. Viral crude lysates were prepared by three rounds of freeze-thaw and viral titers were determined by HPLC. Following infection, 293, PerC6, E1A/E1B Clone 51 and Clone139 cells were passaged twice a week. Ad-GM production was tested at passage 1, 10, and 20 (weeks 1, 5, 10). Results showed that Clones 51 and 139 were able to produce E1-defective virus at levels comparable to PerC6 and 293 cells and that viral production by Clone 51 and Clone139 cells lines was stable (FIG. 3).

Production of oncolytic virus using cell lines derived from E1A/E1B complementing clones. A549 cells, 293 cells and cells derived from E1A/E1B Clones 51 and 139 were grown and infected with 4 replication competent (oncolytic) adenoviruses (CG8900, CG8840, OV945 and OV1025) for 3–4 hrs at an M.O.I. of 2. After 72 hrs the supernatant was harvested and used to infect 293 cells at different dilutions in a standard plaque assay. Infection was allowed to proceed for 4 hrs, and then the cells were cultured in agarose medium for 8–11 days. The results are shown in Table 4. CG8900, CG8840, OV945 and OV1024 are replication competent adenoviral vectors comprising cell type specific transcriptional regulatory elements controlling E1A and E1B.

TABLE 4

Oncolytic Virus Infection of A549, 293 and
E1A/E1B Complementing Cell Lines.

| | Virus Yield (Pfu/cell) | | | |
|---|---|---|---|---|
| | CG8900 | CG8840 | OV945 | OV1025 |
| A549 | 1.20E+03 | 8.00E+01 | 1.20E+03 | 2.40E+03 |
| 293AAV | 2.80E+03 | 2.80E+03 | 4.00E+03 | 4.80E+03 |
| Clone 51 | 4.00E+04 | 3.20E+04 | 1.20E+04 | 4.00E+03 |
| Clone 139 | 1.60E+04 | 4.00E+03 | 8.00E+03 | 1.80E+04 |

Southern blot analysis of Clones 51 and 139 for E1A/E1B sequences in early and late passage cells. DNA from early and late passage cultures of Clone 51, Clone 139 and 293 cells was digested with BamH I which cuts once within the vector and analyzed with E1A (nts 827–1340) or E1B (nts 2805–3329) specific probes by Southern blot (FIGS. 4A and B). The blots show stable integration of E1A and E1B genes in both early and late passage cells. Clone 139 appears to have two copies of the E1A gene and one copy of E1B. Clone 51 has four copies (upper band is a doublet) of E1A and two copies of E1B. Asterisks indicate relevant bands.

Figure 5:
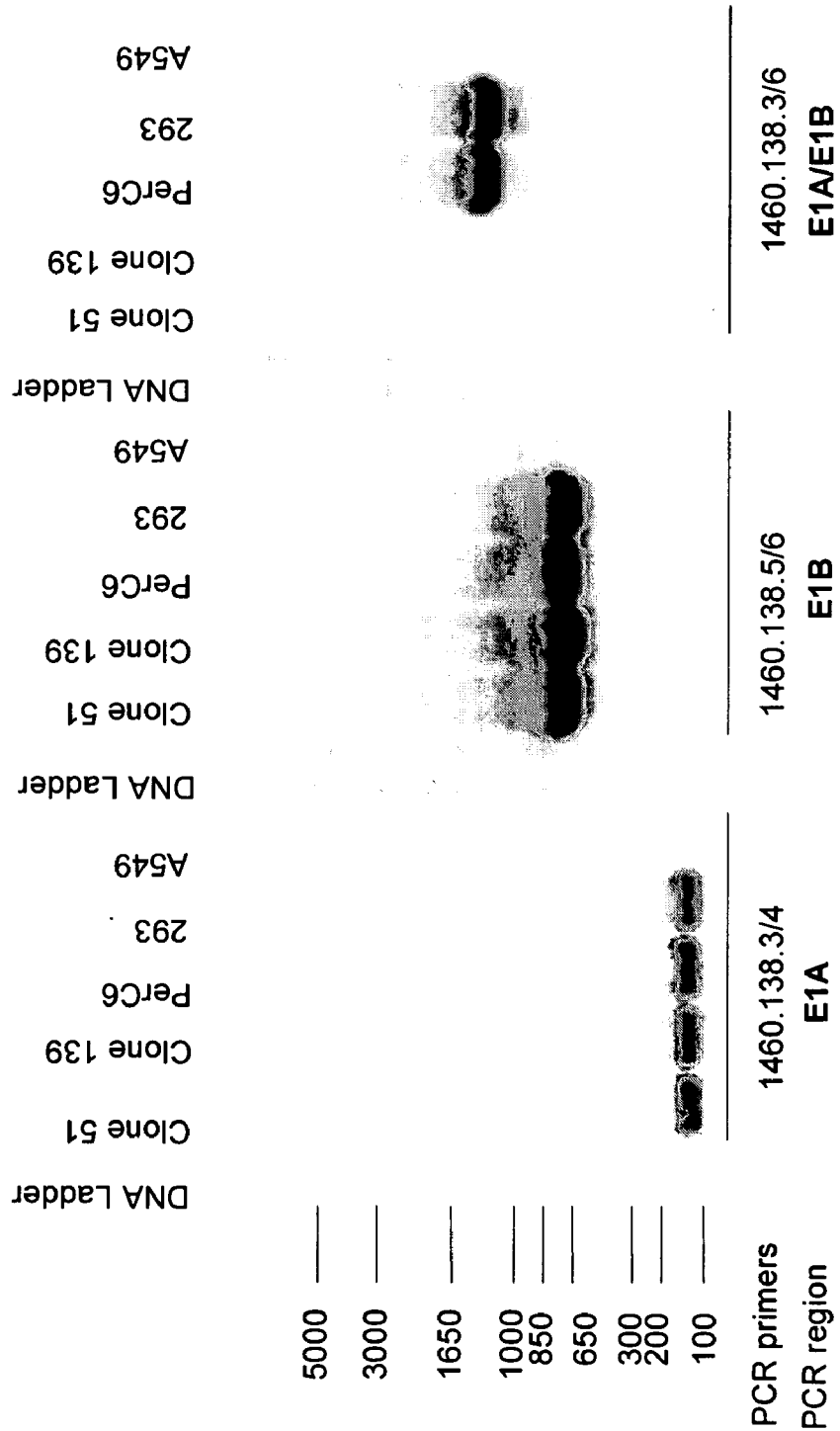
FIG. 5 illustrates the results of Southern blots of DNA from Clones 51 and 139, PerC6, 293 and A549 cells probed using PCR primers specific for E1A (1460.138.3/4), E1B (1460.138.5/6) and continuous E1A–E1B sequences (1460.138.3/6).

Characterization of Genomic Integration in Packaging Cell Lines. The separate expression vectors utilized for co-transduction of the E1A and E1B genes should integrate into the host cell genome at different locations, which serves to further reduce any possibility of recombination between a replication defective Ad vector and the packaging cell lines of the present invention. DNA from Clones 51 and 139, 293 and PerC6 cells was probed by PCR with primers specific for E1A, E1B and continuous E1A–E1B sequences (FIG. 5). Primer 1460.138.3/4 (1460.138.3: 5' TGT GTC TAG AGA ATG CM TAG 3' (SEQ ID NO:9); 1460.138.4: 5' GAT ATA TGT CGA CTG GCC TGG GGC GTT TAC AGC 3'(SEQ ID NO:10)) amplifies nts 1338 to 1542 of the Ad5 genome at the c-terminal end of the E1A coding region, and primer 1460.138.5/6 (1460.138.5: 5' GAC ATG CGT CGA CAT GGA GCG MG MA CCC ATC TG 3' (SEQ ID NO:11); 1460.138.6: 5' CCA TAG MG CTT ACA CCG TGT AG 3' (SEQ ID NO:12)) amplifies nts 2019 to 2815, the majority of the E1B 55k open reading frame. The results of Southern blots from all four cell lines indicated that the expected individual E1A and E1B fragments were present. If the Ad5 genome from the E1A C-terminus through E1B 55k is intact and continuous as in the 293 and PerC6 cell lines, 1460.138.3/6 will amplify the 1477 base pair region from nts 1338 to 2815. The results of Southern blots of DNA derived from 293 and PerC6 cell lines indicated the presence of the 1477 base pair region. In contrast, the results of Southern blots of DNA derived from Clones 51 and 139, did not show the 1477 base pair region confirming that a continuous E1A/E1B genome is not present in the clones.

Figures 6A, 6B:
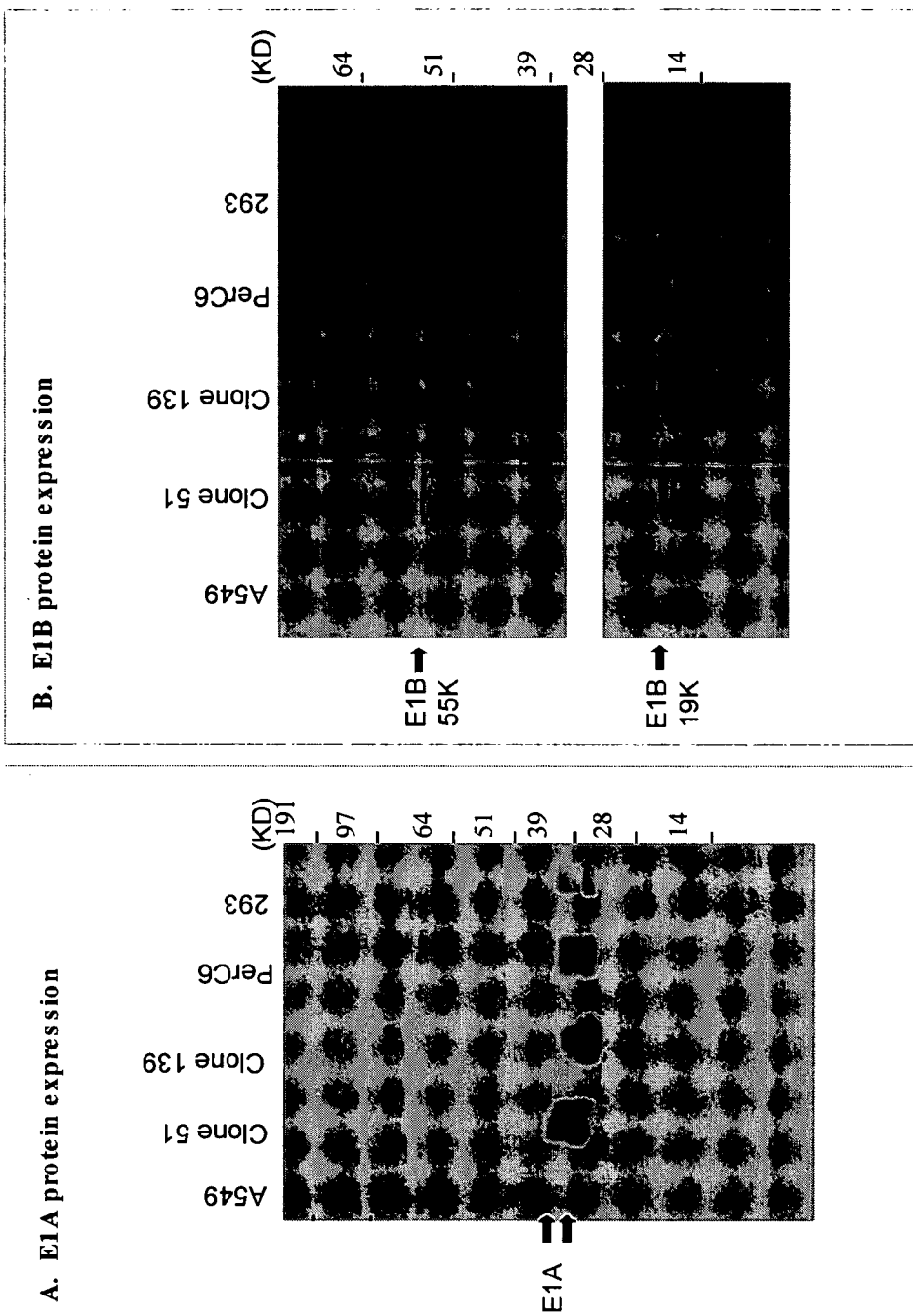
FIGS. 6A and B depict the results of Western blot analysis performed using lysates of A549 cells, Clone 51 cells, Clone 139 cells, PerC6 cells and 293 cells probed with a monoclonal antibody directed against E1A, E1B 19K or E1B 55k.

Protein Analysis of Clones 51 and 139. Western blot analysis was performed using methods widely employed in the art (e.g., Anton and Graham, J. Virology, 69, 4600–4606, 1995, Sambrook and Russell, supra). 293, PerC6, A549, A549 clone 51, and A549 clone 139 cells were plated in 10 cm tissue culture dishes. 72 hours later cells were scraped into the supernatant, pelleted, and resuspended in lysis buffer (100 mM NaCl, 20 mM Tris ph 7.5, 10 mM EDTA, 1% deoxycholic acid) supplemented with a complete, mini protease inhibitor cocktail (Roche). Protein concentrations of samples were assessed with a protein assay kit (Bio-Rad). For detection of E1A (FIG. 6A) 10 mg of total protein for each sample was loaded onto a 4–12% NuPage Novex Bis-Tris SDS-PAGE gel (Invitrogen) and fractionated in NuPage MOPS running buffer. Fractions were transferred to an Invitrolon PVDF membrane (Invitrogen), which was probed with a monoclonal E1A primary antibody (Neomarkers) and a horseradish peroxidase conjugated secondary antibody. Bound antibody complexes were detected with enhanced chemiluminescence (Amersham). Detection of E1B 19K and E1B 55K was performed as above (FIG. 6B), with the following exceptions. Twenty-five micrograms of total protein from each sample were fractionated. The primary antibodies used were monoclonals against E1B 19K and E1B 55K (Oncogene Research Products). The results indicated that Clones 51 and 139 have levels of E1A (38 and 46 kD) expression essentially equivalent to that of PerC6, and greater than that detected for 293 cells. E1B 19 kD production in the two clones are also comparable to levels detected from 293 and PerC6 cells.

Figure 7:
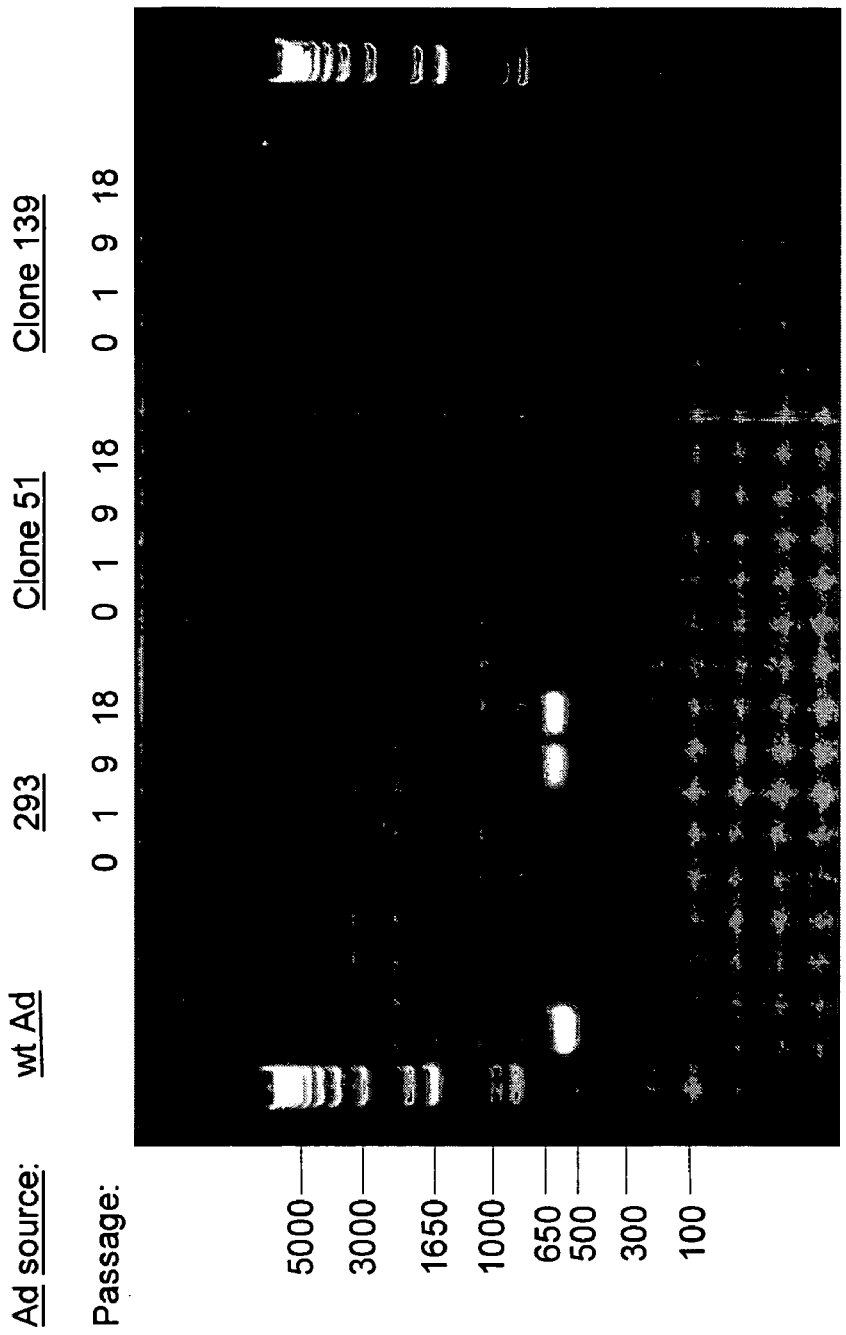
FIG. 7 illustrates the results of an RCA detection assay wherein DNA purified from lysates of wildtype adenovirus (wt Ad), 293 cells, Clone 51 and Clone 139 was amplified by PCR using primers specific to E1A (nts 133–696).

RCA Detection Assay. An RCA study was done to compare Clone 51 and 139 cells with 293 and PerC6 cells, cell lines traditionally used for large scale production of adenovirus (Gao et al., 2000, Hum Gene Therapy 11:213; Murakami et al., 2002, Hum Gene Thera 13:909; Kim et al., 2001, Exp Mol Med 33:145). Each cell type was used to passage a purified E1-deleted Ad GM-CSF virus stock for up to 20 passages. Clone 51, Clone 139, and 293 cells were infected with E1-deleted GM-CSF virus at MOI=75. After 72 hours, crude lysates were prepared, titered by HPLC and used for the second round of infection on naïve cells of the same type (293 lysates on naïve 293 cells, etc.). Equal numbers of particles were used for each infection. This infection cycle was repeated 18 times. Adenoviral DNA was purified from lysates at infection cycle 1, 9, and 18 and amplified by PCR using primers specific to E1A (nts 133–696) region (FIG. 7). The expected PCR product is about 0.56 Kb. The PCR primers used for the RCA assay were: 66.114.2: 5'-GTGGCGGMCACATGTAAGCG-3' (SEQ ID NO:13) and 49.17.2: 5'-AGTTCGTGAAGGG-TAGGTGGTTC-3 (SEQ ID NO:14). E1A sequences (due to RCA) were detected in the 293 cell-derived passage by cycle 9. Adenovirus from Clones 51 and 139 were negative for E1A sequences through cycle 18.

The invention is not to be limited in scope by the recombinant expression vectors and cell lines exemplified, which are intended as illustrations of one aspect of the invention. It is to be understood that the above detailed examples and described embodiments are intended to illustrate and not limit the scope of the invention. Other aspects, advantages and modifications within the scope of the invention will be apparent to those skilled in the art to which the invention pertains.

What is claimed is:

1. An adenovirus packaging cell line permissive for replication of an E1A/E1B deficient adenovirus vector, wherein said cell line comprises an adenovirus E1A coding sequence, each and an adenovirus E1B coding sequence operably linked to a promoter that lacks substantial sequence identity to a native adenovirus E1A or E1B promoter, and wherein said adenovirus E1A coding sequence and said adenovirus E1B coding sequence are stably integrated into said cell line and are operably linked to different heterologous promoters.

2. The adenovirus packaging cell line of claim 1, wherein said adenovirus E1A coding sequence and said adenovirus E1B coding sequence are stably integrated at different sites in said cell line.

3. The adenovirus packaging cell line of claim 1, wherein said heterologous promoters that lack substantial sequence identity with a native adenovirus E1A or E1B promoter are retrovirus promoters.

4. The adenovirus packaging cell line of claim 1, wherein said adenovirus E1A coding sequence comprises the sequence set forth in SEQ ID NO:1.

5. The adenovirus packaging cell line of claim 1, wherein said adenovirus E1B coding sequence comprises the sequence set forth in SEQ ID NO:4.

6. The adenovirus packaging cell line of claim 2, wherein said cell line is a human cell line.

7. The adenovirus packaging cell line of claim 6, wherein said cell line is selected from the group consisting of A549 cells permissive for adenovirus replication, PC-3 cells or primary cells permissive for adenovirus production.

8. A method of producing an adenovirus packaging cell line permissive for replication of an E1A/E1B deficient adenovirus vector, the method comprising: introducing into a cell line permissive for adenovirus replication, nucleic acid comprising (i) an adenovirus E1A coding sequence operably linked to a promoter that lacks substantial sequence identity with a native adenovirus E1A or E1B promoter and (ii) an adenovirus E1B coding sequence operably linked to a promoter that lacks substantial sequence identity with a native adenovirus E1A or E1B promoter, wherein the nucleic acid comprising the adenovirus E1A coding sequence and the nucleic acid comprising the adenovirus E1B coding sequence are present on separate vectors and the promoters operably liked to the E1A and E1B coding sequences are different.

9. The method according to claim 8, wherein one of the separate vectors is a retroviral expression vector.

10. The method according to claim 8, wherein each of the separate vectors is a retroviral expression vector.

* * * * *